(12) United States Patent
Ruddock et al.

(10) Patent No.: US 9,416,388 B2
(45) Date of Patent: Aug. 16, 2016

(54) METHOD FOR PRODUCING DISULFIDE BOND CONTAINING PROTEINS IN A PROKARYOTIC CYTOPLASM

(75) Inventors: Lloyd Ruddock, Oulu (FI); Feras Hatahet, Boston, MA (US)

(73) Assignee: University of Oulu, Oulu (FI)

( * ) Notice: Subject to any disclaimer, the term of this patent is extended or adjusted under 35 U.S.C. 154(b) by 0 days.

(21) Appl. No.: 13/983,473

(22) PCT Filed: Feb. 3, 2012

(86) PCT No.: PCT/FI2012/050105
§ 371 (c)(1),
(2), (4) Date: Aug. 1, 2014

(87) PCT Pub. No.: WO2012/104494
PCT Pub. Date: Aug. 9, 2012

(65) Prior Publication Data
US 2014/0342398 A1   Nov. 20, 2014

(30) Foreign Application Priority Data
Feb. 4, 2011   (FI) ........................... 20115115

(51) Int. Cl.
C12P 21/06   (2006.01)
C12N 9/02   (2006.01)
C12P 21/00   (2006.01)
C12N 15/70   (2006.01)

(52) U.S. Cl.
CPC ............ *C12P 21/00* (2013.01); *C12N 9/0051* (2013.01); *C12N 9/0083* (2013.01); *C12N 15/70* (2013.01); *Y02P 20/52* (2015.11)

(58) Field of Classification Search
None
See application file for complete search history.

(56) References Cited

U.S. PATENT DOCUMENTS

2007/0254334 A1   11/2007   Beckwith et al.

FOREIGN PATENT DOCUMENTS

| EP | 0992588 A1 | 4/2000 |
| WO | WO2007127735 A2 | 11/2007 |
| WO | WO2010056901 A2 | 5/2010 |
| WO | WO2010139585 A1 | 12/2010 |

OTHER PUBLICATIONS

Beltzer J.P. et al., Charged Residues Are Major Determinants of the Transmembrane Orientation of a Signal-Anchor Sequence*, The Journal of Biological Chemistry, Jul. 9, 1990, pp. 973-978, vol. 266, No. 2, Issue of Jan. 5, 1991, The American Society for Biochemistry and Molecular Biology, Inc., USA.
Dutton, R.J. et al., Inhibition of Bacterial Disulfide Bond Formation by the Anticoagulant Warfarin, http://www.pnas.org/content/107/1/297, Proceedings of the National Academy of Sciences of the, United States of America, Published online on Dec. 15, 2009, pp. 297-301, vol. 107, No. 1, Issue of Jan. 5, 2010.
Hatahet et al., Disruption of reducing pathways is not essential for efficient disulfide bond formation in the cytoplasm of *E. coli*, Microbial Cell Factories, http://www.microbialcellfactories.com/content/67, Sep. 13, 2010, pp. 67, vol. 9, No. 1, BioMed Central Ltd.
Kadokura et al.,Four cysteines of the membrane protein DsbB act in concert to oxidize its substrate DsbA, The EMBO Journal, 2002, pp. 2354-2363, vol. 21 No. 10 , European Molecular Biology Organization.
Kenji Inaba, Disulfide Bond Formatton System in *Escherichia coli*, Journal of Biochemistry, Nov. 1, 2009, pp. 591-597, vol. 146, No. 5, Published by Oxford University Press on behalf of the Japanese Biochemical Society.
Van Dat Nguyen et al., Pre-expression of a sulfhydryl oxidase significantly increases the yields of eukaryotic disulfide bond containing proteins expressed in the cytoplasm of *E.coli*, Microbial Cell Factories, http://www.microbialcelifactories.com/content/10/1/1, Jan. 7, 2011, pp. 1-13, vol. 10, No. 1, BioMed Central Ltd. London.
Dalbey et al., Evolutionarily Related Insertion Pathways of Bacterial, Mitochondrial, and Thylakoid Membrane Proteins, Annual Review of Cell and Developmental Biology, www/annualreviews.org., 2000, pp. 51-87, vol. 16, No. 1, European Patent Office.
Weikai Li et al., Structure of a bacterial homologue of vitamin K epoxide reductase, Jan. 28, 2010, Nature, pp. 507-513, vol. 463, No. 7280, Macmillan Publishers limited.
PCT/FI2012/050105 International Search Report, Jun. 5, 2012, pp. 1-15.

*Primary Examiner* — Nancy T Vogel
(74) *Attorney, Agent, or Firm* — Berggren Inc.

(57) ABSTRACT

The present invention relates to a method for producing natively folded disulfide bond containing proteins in a prokaryotic host. The method comprises that in the cytoplasm of a prokaryotic cell is expressed protein(s) of interest that naturally contain disulfide bonds and naturally occurring or inverted transmembrane enzyme, wherein the cysteines of the active site(s) are naturally or after genetic engineering located towards the prokaryotic cytoplasm. The enzyme is selected from the group of VKOR, inverted VKOR (iVKOR) and inverted Dsb B (iDsb B). In the prokaryotic cell is also expressed cytoplasmic DsbA or a corresponding protein being capable of providing electrons to the active site(s) of VKOR, iVKOR or iDsbB. The invention relates also to a prokaryotic host cell and a vector system for producing natively folded disulfide bond containing proteins.

20 Claims, 6 Drawing Sheets

SEQUENCE LISTING

<160> NUMBER OF SEQ ID NOS: 21

<210> SEQ ID NO 1
<211> LENGTH: 178
<212> TYPE: PRT
<213> ORGANISM: Escherichia coli

<400> SEQUENCE: 1

```
Met Ile Met Leu Arg Phe Leu Asn Gln Cys Ser Gln Gly Arg Gly Ala
1               5                   10                  15

Trp Leu Leu Met Ala Phe Thr Ala Leu Ala Leu Glu Leu Thr Ala Leu
            20                  25                  30

Trp Phe Gln His Val Met Leu Leu Lys Pro Cys Val Leu Cys Ile Tyr
        35                  40                  45

Glu Arg Cys Ala Leu Phe Gly Val Leu Gly Ala Ala Leu Ile Gly Ala
    50                  55                  60

Ile Ala Pro Lys Thr Pro Leu Arg Tyr Val Ala Met Val Ile Trp Leu
65                  70                  75                  80

Tyr Ser Ala Phe Arg Gly Val Gln Leu Thr Tyr Glu His Thr Met Leu
                85                  90                  95

Gln Leu Tyr Pro Ser Pro Phe Ala Thr Cys Asp Phe Met Val Arg Phe
            100                 105                 110

Pro Glu Trp Leu Pro Leu Asp Lys Trp Val Pro Gln Val Phe Val Ala
        115                 120                 125

Ser Gly Asp Cys Ala Glu Arg Gln Trp Asp Phe Leu Gly Leu Glu Met
    130                 135                 140

Pro Gln Trp Leu Leu Gly Ile Phe Ile Ala Tyr Leu Ile Val Ala Val
145                 150                 155                 160

Leu Val Val Ile Ser Gln Pro Phe Lys Ala Lys Lys Arg Asp Leu Phe
                165                 170                 175

Gly Arg
```

<210> SEQ ID NO 2
<211> LENGTH: 176
<212> TYPE: PRT
<213> ORGANISM: Escherichia coli

<400> SEQUENCE: 2

```
Met Leu Arg Phe Leu Asn Gln Cys Ser Gln Gly Arg Gly Ala Trp Leu
1               5                   10                  15

Leu Met Ala Phe Thr Ala Leu Ala Leu Glu Leu Thr Ala Leu Trp Phe
            20                  25                  30

Gln His Val Met Leu Leu Lys Pro Cys Val Leu Cys Ile Tyr Glu Arg
        35                  40                  45

Cys Ala Leu Phe Gly Val Leu Gly Ala Ala Leu Ile Gly Ala Ile Ala
    50                  55                  60

Pro Lys Thr Pro Leu Arg Tyr Val Ala Met Val Ile Trp Leu Tyr Ser
65                  70                  75                  80

Ala Phe Arg Gly Val Gln Leu Thr Tyr Glu His Thr Met Leu Gln Leu
                85                  90                  95

Tyr Pro Ser Pro Phe Ala Thr Cys Asp Phe Met Val Arg Phe Pro Glu
            100                 105                 110
```

-continued

Trp Leu Pro Leu Asp Lys Trp Val Pro Gln Val Phe Val Ala Ser Gly
         115                 120                 125

Asp Cys Ala Glu Arg Gln Trp Asp Phe Leu Gly Leu Glu Met Pro Gln
130                 135                 140

Trp Leu Leu Gly Ile Phe Ile Ala Tyr Leu Ile Val Ala Val Leu Val
145                 150                 155                 160

Val Ile Ser Gln Pro Phe Lys Ala Lys Lys Arg Asp Leu Phe Gly Arg
                165                 170                 175

<210> SEQ ID NO 3
<211> LENGTH: 173
<212> TYPE: PRT
<213> ORGANISM: Aeromonas Salmonicida

<400> SEQUENCE: 3

Met Ile Glu Phe Leu Arg Arg Ile Ala Ala His Arg Leu Ala Trp Gly
1               5                   10                  15

Leu Leu Ala Ala Ser Ala Leu Phe Leu Glu Leu Ser Ala Leu Phe Phe
                20                  25                  30

Gln Tyr Val Leu Gly Leu His Pro Cys Val Met Cys Val Tyr Glu Arg
            35                  40                  45

Leu Ala Ile Leu Gly Val Leu Ser Ala Gly Leu Leu Gly Met Val Ala
50                  55                  60

Pro Glu Lys Trp Tyr Leu Arg Trp Ser Ala Leu Leu Leu Trp Gly Tyr
65                  70                  75                  80

Ser Ala Phe Arg Gly Leu Gln Leu Ala Leu Lys His Val Asp Tyr Gln
                85                  90                  95

Met Asn Pro Ser Pro Phe Asn Val Cys Ser Pro Phe Ala Asp Phe Pro
            100                 105                 110

Ser Trp Ala Pro Leu Asp Gln Trp Leu Pro Trp Leu Phe Phe Pro Asp
        115                 120                 125

Gly Asp Cys Ser Glu Ile Ser Trp Gln Phe Leu Ser Phe Ser Met Pro
130                 135                 140

Gln Trp Leu Val Ala Ile Phe Ala Ala Tyr Leu Leu Val Phe Val Val
145                 150                 155                 160

Val Thr Ile Gly Asn Leu Val Lys Gly Arg Cys Cys Ser
                165                 170

<210> SEQ ID NO 4
<211> LENGTH: 196
<212> TYPE: PRT
<213> ORGANISM: Azospirillum sp.

<400> SEQUENCE: 4

Met Gly Val Ala Asp Gly Trp Pro Asn Gly Ser Ala Arg Ala Asn Leu
1               5                   10                  15

Ser Ala Met Met Ile Gln Thr Leu Leu Ser Arg Val Phe Asp Asp Pro
                20                  25                  30

Arg Ile Ala Ala Pro Leu Leu Ala Leu Ala Ser Ala Gly Val Leu Leu
            35                  40                  45

Ser Ala Leu Phe Phe Gln Phe Val Leu Gly Tyr Gln Pro Cys Val Leu
        50                  55                  60

Cys Ile Met Gln Arg Trp Pro Tyr Val Ala Val Met Ala Leu Gly Leu
65                  70                  75                  80

Val Thr Trp Leu Phe Arg Arg Trp Arg Gly Val Gly Asp Ala Leu Leu
                85                  90                  95

```
Val Val Ser Gly Leu Ala Leu Ala Gly Ala Gly Ile Ala Ala Tyr
            100                 105                 110

His Val Gly Val Glu Gln His Trp Ala Gly Thr Ser Ser Cys Gly
            115                 120                 125

Gly Ser Ala Pro Ala Asn Ser Leu Glu Ala Leu Arg Ala Gln Val Leu
130                 135                 140

Ala Ala Pro Val Thr Arg Cys Asp Glu Val Ala Trp Ser Leu Phe Gly
145                 150                 155                 160

Ile Ser Met Ala Gly Tyr Asn Val Val Ile Ser Leu Ala Leu Ala Ala
                165                 170                 175

Tyr Ala Phe Ile Ala Ala Arg Ile Ala Tyr Thr Arg Pro Val Ser
                180                 185                 190

Arg Thr Ala Leu
        195

<210> SEQ ID NO 5
<211> LENGTH: 174
<212> TYPE: PRT
<213> ORGANISM: Rhodoferax ferrireducens

<400> SEQUENCE: 5

Met Ser Phe Gln Val Val Thr Gly Trp Leu Asp Asn Ser Pro Arg Arg
1               5                   10                  15

Ile Phe Ala Phe Val Ser Leu Ala Ser Ile Gly Met Leu Ala Phe Gly
                20                  25                  30

Gln Tyr Leu Gln His Val Gly Leu Glu Pro Cys Pro Met Cys Ile
            35                  40                  45

Val Gln Arg Tyr Ala Leu Val Leu Val Ala Ile Ile Ala Gly Leu Thr
 50                 55                  60

Gly Ala Ser Gly Arg Lys Gly Leu His Leu Gly Ala Val Leu Met
 65                 70                  75                  80

Leu Gly Ser Ser Gly Phe Gly Ala Tyr Val Ala Ala Arg Gln Ser Trp
                85                  90                  95

Leu Gln Trp Tyr Pro Pro Glu Val Val Ser Cys Gly Arg Asp Phe Tyr
            100                 105                 110

Gly Met Ile Glu Thr Phe Pro Leu Gln Arg Ala Ile Pro Met Ile Phe
            115                 120                 125

Lys Gly Ser Gly Asp Cys Ser Lys Val Asp Trp Thr Phe Leu Gly Gly
        130                 135                 140

Ser Ile Ala Asn Trp Thr Phe Val Val Phe Gly Leu Ile Val Leu Leu
145                 150                 155                 160

Ser Leu Ala Leu Ile Trp Arg Arg Val Ser Arg Arg Val Ser
                165                 170

<210> SEQ ID NO 6
<211> LENGTH: 170
<212> TYPE: PRT
<213> ORGANISM: Burkholderia cenocepacia

<400> SEQUENCE: 6

Met Asn Asp Tyr Thr Leu Ala Leu Arg Arg Glu Arg Arg Leu Leu Met
1               5                   10                  15

Leu Leu Gly Trp Val Cys Ile Ala Leu Leu Ala Gly Ala Leu Tyr Leu
                20                  25                  30

Gln Tyr Val Lys Asn Glu Asp Pro Cys Pro Leu Cys Ile Ile Gln Arg
            35                  40                  45
```

```
Tyr Phe Phe Cys Ala Ile Gly Ile Phe Ala Phe Leu Ala Ala Gly Ile
     50                  55                  60

Arg Asn Trp Arg Gly Val Trp Val Leu Glu Leu Leu Ile Ala Ile Ala
 65                  70                  75                  80

Ala Ala Gly Gly Val Gly Thr Ala Ala Arg His Leu Ser Ile Gln Met
                 85                  90                  95

Asn Pro Gly Phe Ser Cys Gly Phe Asp Thr Leu Gln Pro Ile Val Asp
                100                 105                 110

Ser Leu Pro Pro Ala Gln Trp Phe Pro Gly Met Phe Lys Val Ala Gly
            115                 120                 125

Leu Cys Glu Thr Val Tyr Pro Pro Ile Phe Gly Ile Leu Leu Pro Gly
            130                 135                 140

Trp Ala Leu Ile Gly Phe Ala Val Ile Leu Val Ala Val Val Ala Ser
145                 150                 155                 160

Leu Trp Arg His Arg Arg Lys Leu Ala Ser
                165                 170

<210> SEQ ID NO 7
<211> LENGTH: 171
<212> TYPE: PRT
<213> ORGANISM: Pseudoalteromonas atlantica

<400> SEQUENCE: 7

Met Thr Phe Ile Ser Asn Leu Ala Asp Thr Arg Leu Ala Trp Gly Leu
  1               5                  10                  15

Leu Phe Leu Ser Ala Leu Val Leu Val Ala Tyr Ala Leu Phe Ser Gln
                 20                  25                  30

His Ala Met Gly Leu Gln Pro Cys Ile Met Cys Ile Tyr Gln Arg Thr
             35                  40                  45

Ala Ile Phe Gly Ile Met Phe Ala Cys Val Pro Val Leu Ala Ala Asn
 50                  55                  60

Asn Met Leu Thr Arg Leu Phe Ala Phe Thr Val Trp Gly Ile Ser Ala
 65                  70                  75                  80

Ile Trp Gly Gly Leu Ile Ala Trp Glu His Tyr Asp Ile Gln Asn Ala
                 85                  90                  95

Ala Asn Pro Phe Phe Ala Thr Cys Glu Ile Val Pro Asn Phe Pro Ser
                100                 105                 110

Trp Leu Pro Leu His Glu Trp Leu Pro Asn Leu Phe Ala Ala Thr Gly
            115                 120                 125

Asp Cys Gly Asn Ile Asp Trp Val Phe Met Asp Met Ser Met Pro Gln
            130                 135                 140

Trp Met Met Val Val Phe Ala Ile Tyr Ser Ser Ile Trp Phe Val Val
145                 150                 155                 160

Leu Ala Ser Arg Leu Ile Gly Asn Arg Ala Ile
                165                 170

<210> SEQ ID NO 8
<211> LENGTH: 145
<212> TYPE: PRT
<213> ORGANISM: Aeropyrum pernix

<400> SEQUENCE: 8

Met Ser Arg Leu Ser His Ala Leu Leu Ala Val Thr Leu Val Gly Tyr
  1               5                  10                  15

Ala Ala Ser Ile Ala Gly Tyr Phe Glu Tyr Val Ser Gly Ser Gly Val
                 20                  25                  30
```

Cys Glu Ile Gly Asp Val Gly Phe Ala Val Val Asn Cys Ser Ser Val
            35                  40                  45

Tyr Asp Ile Pro Glu Ala Val Val Phe Gly Val Val His Leu Ser Val
    50                  55                  60

Leu Ala Pro Val Tyr Phe Thr Leu Leu Ser Leu Val Ala Leu Ala Tyr
65                  70                  75                  80

Trp Ile Arg Arg Ser Arg Ile Phe Leu Ile Ala Ser Ser Phe Leu Ser
                85                  90                  95

Leu Val Gly Val Val Thr Val Pro Tyr Leu Val Tyr Leu Glu Leu Phe
            100                 105                 110

Val Ala Gly Ala Val Cys Leu Trp Cys Thr Val Met His Ile Ser Ile
            115                 120                 125

Leu Leu Ala Phe Ala Leu Ala Ile Val Gly Leu Arg Ile Gly Gly His
        130                 135                 140

Thr
145

<210> SEQ ID NO 9
<211> LENGTH: 245
<212> TYPE: PRT
<213> ORGANISM: Bifidobacterium longum

<400> SEQUENCE: 9

Met Thr Arg Asn Thr Ala Thr Asp Thr Ser Ser Ser Thr Thr Asn Thr
1               5                   10                  15

Thr Pro Leu Gly Leu Ala Glu Ala Arg Pro Leu Ile Gly Trp Arg His
            20                  25                  30

Ser Ala Thr Trp Thr Tyr Leu Ile Met Leu Ile Ala Ser Ala Val Ala
            35                  40                  45

Leu Gly Ala Ser Leu Ile Leu Ser Ala Glu Thr Leu Gln Leu Ala Arg
    50                  55                  60

His Pro Glu Ser Ala Leu Gly Cys Asp Leu Asn Ser Val Val Ser Cys
65                  70                  75                  80

Ser Ala Val Ala Gln Ser Trp Gln Ala Glu Ile Ala Lys Phe Gly Gly
                85                  90                  95

Leu Ser Tyr Pro Asn Ala Phe Phe Gly Ile Ala Ala Glu Ser Val Phe
            100                 105                 110

Ile Thr Ile Ala Val Ile Gly Leu Ala Arg Val Lys Val Pro Arg Trp
        115                 120                 125

Phe Ala Thr Cys Thr Trp Leu Gly Gly Leu Ala Ala Leu Ala Tyr Ser
        130                 135                 140

Tyr Trp Leu Ser Thr Gln Ser Leu Phe Val Ile His Ala Leu Cys Pro
145                 150                 155                 160

Trp Cys Leu Thr Leu Met Phe Ser Thr Thr Ile Gln Phe Met Ala Leu
                165                 170                 175

Ser His Ala Thr Val Ala Val Gln Gly Leu Pro Ser Arg Lys Ala Val
            180                 185                 190

Ala Ala Asp Asp Ser Asp Gly Glu Ala Glu Val Ala Ala Val Pro Ala
        195                 200                 205

Gly Leu Asn Lys Tyr Tyr Arg Leu Asn Ile Asp Leu Met Val Asp Ile
        210                 215                 220

Leu Trp Ile Val Ala Ile Val Val Leu Ile Ile Val Thr Glu Gly Ala
225                 230                 235                 240

Ala Leu Phe Ala Ala

245

<210> SEQ ID NO 10
<211> LENGTH: 163
<212> TYPE: PRT
<213> ORGANISM: Homo sapiens

<400> SEQUENCE: 10

```
Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Trp Ile Leu Phe Phe Val Leu
        115                 120                 125

Tyr Asp Phe Cys Ile Val Cys Ile Thr Thr Tyr Ala Ile Asn Val Ser
    130                 135                 140

Leu Met Trp Leu Ser Phe Arg Lys Val Gln Glu Pro Gln Gly Lys Ala
145                 150                 155                 160

Lys Arg His
```

<210> SEQ ID NO 11
<211> LENGTH: 175
<212> TYPE: PRT
<213> ORGANISM: Danio rerio

<400> SEQUENCE: 11

```
Met Ala Ala Pro Val Leu Arg Val Ser Thr Pro Arg Trp Glu Arg Ile
1               5                   10                  15

Val Arg Leu Leu Val Cys Leu Ser Gly Ile Leu Leu Ser Leu Tyr Ser
            20                  25                  30

Phe His Val Glu Arg Glu Lys Thr Arg Asp Ala Asn Tyr Arg Ala Met
        35                  40                  45

Cys Asp Leu Ser Ser Ser Ile Ser Cys Ser Lys Val Phe Thr Ser Arg
    50                  55                  60

Trp Gly Arg Gly Phe Gly Leu Leu Gly Ser Ile Phe Gly Asn Asp Ser
65                  70                  75                  80

Ala Val Asn Gln Pro Asn Ser Val Tyr Gly Ile Phe Phe Tyr Val Phe
                85                  90                  95

Gln Leu Leu Leu Gly Leu Thr Ala Ser Ala Met Ala Ala Leu Ile Leu
            100                 105                 110

Met Thr Thr Ser Ile Ala Ser Val Met Gly Ser Leu Tyr Leu Gly Tyr
        115                 120                 125

Ile Leu Tyr Phe Val Leu Lys Asp Phe Cys Val Ile Cys Ile Thr Thr
    130                 135                 140

Tyr Ala Leu Asn Phe Ile Leu Phe Val Leu Asn Tyr Lys Arg Leu Val
145                 150                 155                 160
```

Tyr Leu Asn Glu Ala Trp Lys Gln Gln Leu Gln Ala Lys Arg Asp
                165                 170                 175

<210> SEQ ID NO 12
<211> LENGTH: 313
<212> TYPE: PRT
<213> ORGANISM: Synechococcus sp.

<400> SEQUENCE: 12

Met Ala Thr Gln Arg Leu Thr Ser Arg Arg Gln Asp Gln Gly Ser
1               5                   10                  15

Lys Trp Val Arg Ile Val Met Ala Val Leu Ala Thr Gly Val Ile
                20                  25                  30

Asp Thr Gly Ser Ile Thr Leu Lys Phe Trp Gly Val Leu Gly Asp Leu
                35                  40                  45

Thr Cys Pro Met Gly Ala Gly Gly Cys Asp Lys Val Leu Asn Ser Pro
            50                  55                  60

Trp Gly Thr Leu Phe Gln Gly Asp Gly Phe Ser Ile Pro Leu Ser Phe
65                  70                  75                  80

Ser Gly Leu Ile Ala Tyr Leu Ala Val Leu Val Met Ala Val Val Pro
                85                  90                  95

Leu Leu Pro Gly Leu Ser Glu Asn Lys Ala Asp Leu Ser Arg Arg Thr
                100                 105                 110

Trp Trp Gly Leu Phe Thr Val Ser Leu Val Met Ala Val Phe Ser Leu
                115                 120                 125

Val Leu Val Gly Leu Met Val Ile Lys Ile Gln Ala Phe Cys Phe Phe
130                 135                 140

Cys Val Leu Ser Ala Val Leu Ser Leu Thr Leu Leu Val Leu Ser Leu
145                 150                 155                 160

Ala Gly Gly Gly Trp Asp Asp Pro Ser Gln Leu Leu Phe Arg Gly Phe
                165                 170                 175

Leu Leu Ala Leu Ala Val Leu Leu Gly Gly Leu Ile Trp Ala Ser Val
                180                 185                 190

Leu Asp Pro Ala Arg Pro Asp Ala Val Ala Thr Gly Pro Gly Ala Pro
                195                 200                 205

Pro Pro Val Leu Thr Glu Ser Asn Pro Ala Lys Ile Ser Leu Ala Glu
210                 215                 220

His Leu Thr Ala Ser Gly Ala Val Met Tyr Ser Ala Tyr Trp Cys Pro
225                 230                 235                 240

His Cys His Glu Gln Lys Glu Met Phe Gly Gln Glu Ala Ala Lys Thr
                245                 250                 255

Leu Lys Val Val Glu Cys Ala Pro Thr Gly Gln Asn Asn Glu Ala Lys
                260                 265                 270

Leu Cys Gln Ser Lys Gly Ile Glu Gly Phe Pro Thr Trp Glu Ile Asn
                275                 280                 285

Gly Glu Leu Asp Ser Gly Val Lys Lys Leu Pro Glu Leu Ala Arg Leu
                290                 295                 300

Ser Gly Tyr Gln Gly Ser Lys Asp Phe
305                 310

<210> SEQ ID NO 13
<211> LENGTH: 398
<212> TYPE: PRT
<213> ORGANISM: Anaeromyxobacter sp.

<400> SEQUENCE: 13

```
Met Thr Arg Asp Arg Lys Lys Lys Pro Asp Arg Arg Pro Ser Ala Pro
1               5                   10                  15

Thr Pro Ala Pro Pro Arg Ala Ala Leu Leu Val Ala Ser Leu Leu Leu
            20                  25                  30

Ala Leu Gly Gly Val Ala Leu Ser Val Ala Leu Ala Arg Leu His Ala
        35                  40                  45

Arg Ala His Ala Gly Leu Ser Ser Phe Cys Ala Ile Asn Asp Val Val
    50                  55                  60

Asn Cys Asp Arg Val Ala Leu Ser Arg Phe Ser Thr Phe Leu Gly Leu
65                  70                  75                  80

Pro Val Ala Leu Trp Gly Ala Leu Gly Tyr Gly Leu Ala Ala Val Leu
                85                  90                  95

Ala Ala Arg Ala Leu Ala His Ala Arg Arg Gly Val Thr Ala Ala Arg
            100                 105                 110

Gly Leu Leu Phe Ala Val Ala Ala Val Ala Val Ala Ala Ser Ala Ala
        115                 120                 125

Leu Ala Val Val Ser Glu Leu Ala Ile Gly Ala Trp Cys Leu Leu Cys
    130                 135                 140

Met Ala Ser Trp Ala Thr Ala Ala Gly Leu Leu Ala Thr Ala Trp Arg
145                 150                 155                 160

Ala Cys Pro Ser Gly Pro Ala Ala Val Ala Ala Asp Val Ala Val
                165                 170                 175

Leu Arg Ala Arg Pro Ala Arg Thr Ala Ala Leu Ala Leu Val Ala Leu
            180                 185                 190

Val Ala Val Gly Ala Arg Ala Ala Tyr Ala Arg Tyr Ala Ala Thr
        195                 200                 205

Val Pro Arg Ala Pro Ala Ala Ser Ala Gly Ala Arg Ala Pro Gly Pro
210                 215                 220

Ile Ser Pro Ala Pro Val Ala Ala Gly Gly Val Val Val Glu Phe Ser
225                 230                 235                 240

Asp Tyr Glu Cys Pro Phe Cys Ala Arg Ala His Glu Gln Leu Ala Thr
                245                 250                 255

Leu Arg Ala Ala Arg Pro Asp Leu Glu Ile Val Arg Arg His Phe Pro
            260                 265                 270

Leu Asp Ala Ala Cys Asn Pro Ala Leu Ala Arg Ser Ile His Pro Ser
        275                 280                 285

Ala Cys Ala Leu Ala Arg Ala Ala Ile Cys Ala Glu Ala Gln Gly Arg
    290                 295                 300

Phe Ala Glu Met Asp Asp Ala Leu Phe Arg Asn Gln Gln Ala Arg Glu
305                 310                 315                 320

Pro Ala Ser Arg Leu Ala Ala Arg Leu Gly Leu Asp Val Ala Ala Phe
                325                 330                 335

Glu Ala Cys Leu Ala Ser Pro Ala Thr Glu Ala Arg Leu Ala Arg Asp
            340                 345                 350

Val Glu Asp Gly Met Arg Ala Gly Val Arg Ala Thr Pro Ser Tyr Val
        355                 360                 365

Val Gly Gly Lys Val Tyr Ala Gly Glu Leu Pro Pro Gly Leu Leu Ala
    370                 375                 380

Ala Pro Ala Ala Pro Ala Pro Pro Arg Ala Ala Glu Arg
385                 390                 395

<210> SEQ ID NO 14
<211> LENGTH: 147
```

```
<212> TYPE: PRT
<213> ORGANISM: Aeropryum pernix

<400> SEQUENCE: 14

Met Val Glu Ala Arg Leu Leu Asp Ala Leu Tyr Leu Ala Ala Leu Ala
1               5                   10                  15

Val Gly Trp Leu Ala Ser Ile Gly Gly Phe Ile Glu Phe Arg Arg Ser
            20                  25                  30

Leu Leu Gly Gly Gly Phe Val Cys Lys Ala Asp Ala Lys Gly Trp Ile
        35                  40                  45

Asn Cys Arg Ser Ala Tyr Val Ile Pro Gln Ala Phe Ile Ala Gly Arg
    50                  55                  60

Ile His Leu Ser Glu Leu Ala Pro Ile Tyr Phe Thr Ala Thr Leu Ala
65                  70                  75                  80

Thr Ala Val Leu Gly Val Leu Leu Asp Ile Asp Leu Ala Lys Leu
                85                  90                  95

Ser Tyr Leu Leu Ala Ala Gly Ala Ala Ser Val Pro Tyr Leu Val
                100                 105                 110

Tyr Leu Glu Val Arg Val Ala Lys Ala Ile Cys Leu Trp Cys Thr Ile
            115                 120                 125

Met His Leu Ser Ile Ile Leu Ala Val Ala Ser Ala Thr Ala Lys Ile
    130                 135                 140

Leu Gly Gly
145

<210> SEQ ID NO 15
<211> LENGTH: 134
<212> TYPE: PRT
<213> ORGANISM: Pyrobaculum aerophilum

<400> SEQUENCE: 15

Met Ala Leu Tyr Ile Leu Thr Gly Leu Leu Ala Ala Leu Gly Val Ala
1               5                   10                  15

Val Gly Leu Leu Gly Ser Arg Leu Ile Ala Leu Ser Leu Leu Ala Ala
            20                  25                  30

Ala Gly Leu Leu His Thr Leu Phe Asn Lys Pro Ser Ala Phe Cys Ala
        35                  40                  45

Lys Tyr Lys Ile Gly Gly Cys Glu Ala Val Leu Ser Ser Pro Tyr Ala
    50                  55                  60

Arg Pro Phe Gly Ile Pro Leu Glu Tyr Leu Gly Ala Ala Trp Phe Ala
65                  70                  75                  80

Gly Val Pro Ile Ala Tyr Tyr Leu Gly Ile Gly Leu Val Trp Ser Val
                85                  90                  95

Met Ala Phe Ala Gly Val Ile Ala Leu Val Ala Ile Glu Ala Lys Leu
                100                 105                 110

Arg Ala Phe Cys Ile Tyr Cys Thr Val Ala His Val Ile Gly Leu Ala
            115                 120                 125

Ala Ala Phe Leu Leu Leu
    130

<210> SEQ ID NO 16
<211> LENGTH: 190
<212> TYPE: PRT
<213> ORGANISM: Escherichia coli

<400> SEQUENCE: 16

Met Ala Gln Tyr Glu Asp Gly Lys Gln Tyr Thr Thr Leu Glu Lys Pro
```

```
            1               5                  10                 15
          Val Ala Gly Ala Pro Gln Val Leu Glu Phe Phe Ser Phe Phe Cys Pro
                        20                 25                 30
          His Cys Tyr Gln Phe Glu Glu Val Leu His Ile Ser Asp Asn Val Lys
                        35                 40                 45
          Lys Lys Leu Pro Glu Gly Val Lys Met Thr Lys Tyr His Val Asn Phe
                        50                 55                 60
          Met Gly Gly Asp Leu Gly Lys Asp Leu Thr Gln Ala Trp Ala Val Ala
           65                    70                 75                 80
          Met Ala Leu Gly Val Glu Asp Lys Val Thr Val Pro Leu Phe Glu Gly
                                85                 90                 95
          Val Gln Lys Thr Gln Thr Ile Arg Ser Ala Ser Asp Ile Arg Asp Val
                        100                105                110
          Phe Ile Asn Ala Gly Ile Lys Gly Glu Glu Tyr Asp Ala Ala Trp Asn
                        115                120                125
          Ser Phe Val Val Lys Ser Leu Val Ala Gln Gln Glu Lys Ala Ala Ala
                        130                135                140
          Asp Val Gln Leu Arg Gly Val Pro Ala Met Phe Val Asn Gly Lys Tyr
          145                150                155                160
          Gln Leu Asn Pro Gln Gly Met Asp Thr Ser Asn Met Asp Val Phe Val
                        165                170                175
          Gln Gln Tyr Ala Asp Thr Val Lys Tyr Leu Ser Glu Lys Lys
                        180                185                190

<210> SEQ ID NO 17
<211> LENGTH: 217
<212> TYPE: PRT
<213> ORGANISM: Escherichia coli

<400> SEQUENCE: 17

Met Asp Asp Ala Ala Ile Gln Gln Thr Leu Ala Lys Met Gly Ile Lys
           1               5                  10                 15
          Ser Ser Asp Ile Gln Pro Ala Pro Val Ala Gly Met Lys Thr Val Leu
                        20                 25                 30
          Thr Asn Ser Gly Val Leu Tyr Ile Thr Asp Asp Gly Lys His Ile Ile
                        35                 40                 45
          Gln Gly Pro Met Tyr Asp Val Ser Gly Thr Ala Pro Val Asn Val Thr
                        50                 55                 60
          Asn Lys Met Leu Leu Lys Gln Leu Asn Ala Leu Glu Lys Glu Met Ile
           65                    70                 75                 80
          Val Tyr Lys Ala Pro Gln Glu Lys His Val Ile Thr Val Phe Thr Asp
                                85                 90                 95
          Ile Thr Cys Gly Tyr Cys His Lys Leu His Glu Gln Met Ala Asp Tyr
                        100                105                110
          Asn Ala Leu Gly Ile Thr Val Arg Tyr Leu Ala Phe Pro Arg Gln Gly
                        115                120                125
          Leu Asp Ser Asp Ala Glu Lys Glu Met Lys Ala Ile Trp Cys Ala Lys
                        130                135                140
          Asp Lys Asn Lys Ala Phe Asp Asp Val Met Ala Gly Lys Ser Val Ala
          145                150                155                160
          Pro Ala Ser Cys Asp Val Asp Ile Ala Asp His Tyr Ala Leu Gly Val
                        165                170                175
          Gln Leu Gly Val Ser Gly Thr Pro Ala Val Val Leu Ser Asn Gly Thr
                        180                185                190
```

-continued

Leu Val Pro Gly Tyr Gln Pro Pro Lys Glu Met Lys Glu Phe Leu Asp
                195                 200                 205

Glu His Gln Lys Met Thr Ser Gly Lys
    210                 215

<210> SEQ ID NO 18
<211> LENGTH: 492
<212> TYPE: PRT
<213> ORGANISM: Homo sapiens

<400> SEQUENCE: 18

Met Asp Ala Pro Glu Glu Asp His Val Leu Val Leu Arg Lys Ser
1               5                   10                  15

Asn Phe Ala Glu Ala Leu Ala Ala His Lys Tyr Leu Leu Val Glu Phe
                20                  25                  30

Tyr Ala Pro Trp Cys Gly His Cys Lys Ala Leu Ala Pro Glu Tyr Ala
                35                  40                  45

Lys Ala Ala Gly Lys Leu Lys Ala Glu Gly Ser Glu Ile Arg Leu Ala
        50                  55                  60

Lys Val Asp Ala Thr Glu Glu Ser Asp Leu Ala Gln Gln Tyr Gly Val
65                  70                  75                  80

Arg Gly Tyr Pro Thr Ile Lys Phe Phe Arg Asn Gly Asp Thr Ala Ser
                85                  90                  95

Pro Lys Glu Tyr Thr Ala Gly Arg Glu Ala Asp Asp Ile Val Asn Trp
                100                 105                 110

Leu Lys Lys Arg Thr Gly Pro Ala Ala Thr Thr Leu Pro Asp Gly Ala
            115                 120                 125

Ala Ala Glu Ser Leu Val Glu Ser Ser Glu Val Ala Val Ile Gly Phe
        130                 135                 140

Phe Lys Asp Val Glu Ser Asp Ser Ala Lys Gln Phe Leu Gln Ala Ala
145                 150                 155                 160

Glu Ala Ile Asp Asp Ile Pro Phe Gly Ile Thr Ser Asn Ser Asp Val
                165                 170                 175

Phe Ser Lys Tyr Gln Leu Asp Lys Asp Gly Val Val Leu Phe Lys Lys
                180                 185                 190

Phe Asp Glu Gly Arg Asn Asn Phe Glu Gly Glu Val Thr Lys Glu Asn
            195                 200                 205

Leu Leu Asp Phe Ile Lys His Asn Gln Leu Pro Leu Val Ile Glu Phe
        210                 215                 220

Thr Glu Gln Thr Ala Pro Lys Ile Phe Gly Gly Glu Ile Lys Thr His
225                 230                 235                 240

Ile Leu Leu Phe Leu Pro Lys Ser Val Ser Asp Tyr Asp Gly Lys Leu
                245                 250                 255

Ser Asn Phe Lys Thr Ala Ala Glu Ser Phe Lys Gly Lys Ile Leu Phe
                260                 265                 270

Ile Phe Ile Asp Ser Asp His Thr Asp Asn Gln Arg Ile Leu Glu Phe
            275                 280                 285

Phe Gly Leu Lys Lys Glu Glu Cys Pro Ala Val Arg Leu Ile Thr Leu
        290                 295                 300

Glu Glu Glu Met Thr Lys Tyr Lys Pro Glu Ser Glu Glu Leu Thr Ala
305                 310                 315                 320

Glu Arg Ile Thr Glu Phe Cys His Arg Phe Leu Glu Gly Lys Ile Lys
                325                 330                 335

Pro His Leu Met Ser Gln Glu Leu Pro Glu Asp Trp Asp Lys Gln Pro
                340                 345                 350

Val Lys Val Leu Val Gly Lys Asn Phe Glu Asp Val Ala Phe Asp Glu
        355                 360                 365

Lys Lys Asn Val Phe Val Glu Phe Tyr Ala Pro Trp Cys Gly His Cys
    370                 375                 380

Lys Gln Leu Ala Pro Ile Trp Asp Lys Leu Gly Glu Thr Tyr Lys Asp
385                 390                 395                 400

His Glu Asn Ile Val Ile Ala Lys Met Asp Ser Thr Ala Asn Glu Val
                405                 410                 415

Glu Ala Val Lys Val His Ser Phe Pro Thr Leu Lys Phe Phe Pro Ala
            420                 425                 430

Ser Ala Asp Arg Thr Val Ile Asp Tyr Asn Gly Glu Arg Thr Leu Asp
        435                 440                 445

Gly Phe Lys Lys Phe Leu Glu Ser Gly Gln Asp Gly Ala Gly Asp
    450                 455                 460

Asp Asp Asp Leu Glu Asp Leu Glu Glu Ala Glu Glu Pro Asp Met Glu
465                 470                 475                 480

Glu Asp Asp Asp Gln Lys Ala Val Lys Asp Glu Leu
                485                 490

<210> SEQ ID NO 19
<211> LENGTH: 8
<212> TYPE: PRT
<213> ORGANISM: Artificial
<220> FEATURE:
<223> OTHER INFORMATION: tag sequence

<400> SEQUENCE: 19

Met His His His His His His Met
1               5

<210> SEQ ID NO 20
<211> LENGTH: 26
<212> TYPE: PRT
<213> ORGANISM: Artificial
<220> FEATURE:
<223> OTHER INFORMATION: linker

<400> SEQUENCE: 20

Gly Ser Gly Ser Gly Ser Gly Ser Gly Ser Ile Glu Gly Arg Gly Ser
1               5                   10                  15

Gly Ser Gly Ser Gly Ser Gly Ser His Met
            20                  25

<210> SEQ ID NO 21
<211> LENGTH: 26
<212> TYPE: PRT
<213> ORGANISM: Artificial
<220> FEATURE:
<223> OTHER INFORMATION: linker

<400> SEQUENCE: 21

Gly Ser Gly Ser Gly Ser Gly Ser Gly Ser Ile Glu Gly Arg Gly Ser
1               5                   10                  15

Gly Ser Gly Ser Gly Ser Gly Ser His Met
            20                  25

//METHOD FOR PRODUCING DISULFIDE BOND CONTAINING PROTEINS IN A PROKARYOTIC CYTOPLASM

PRIORITY

This application is a national phase application of PCT/FI2012/050105 filed on Feb. 3, 2012 and claiming priority of FI20115115, which was filed on Feb. 4, 2011, and both of which are incorporated herein by reference.

SEQUENCE LISTING

This application contains sequence listing which is provided on written format as well as on a computer readable format, both of which are identical.

FIELD OF THE INVENTION

This invention relates to a method, a host cell and a vector system for producing protein(s) of interest containing one or more disulfide bonds in their native state in a prokaryotic host.

Many proteins and enzymes of biotechnological importance contain structure stabilizing disulfide bonds, with an estimated one third of all human proteins folding in the endoplasmic reticulum (ER) and acquiring disulfide bonds there. This includes most proteins which get secreted or end up on the outer membrane. Since any two cysteine residues in a protein have the potential to form a disulfide bond, the correct formation of native disulfide bonds is not trivial. Hence, it is unsurprising that native disulfide bond formation is often the rate-limiting step in the folding of proteins in vitro and in vivo.

Currently proteins that contain disulfide bonds are difficult for the biotech industry to produce on a large scale. The most common route is to produce these proteins in the cytoplasm of E. coli. There are no mechanisms for disulfide bond formation in the cytoplasm. This, combined with the efficient pathways for disulfide bond reduction in the cytoplasm, means that recombinant proteins which fold in the cytoplasm of bacteria, such as E. coli, lack structural and/or functional disulfides and usually form insoluble, inactive inclusion bodies. Inclusion body refolding is a widely studied and patented field. However, it is costly, complex and generally inefficient.

Alternative routes for producing disulfide bonded proteins in prokaryotes also have drawbacks.

I. Disulfide bond formation in the periplasm. The process of native disulfide bond formation in the periplasm of bacteria is a multi-factorial process, which shows variations between species. Disulfide bond formation (oxidation of a dithiol to a disulfide) is catalysed by the transmembrane proteins DsbB and/or vitamin-K oxidoreductases (VKOR). These have a transmembrane topology which has their active site(s) located on the periplasmic side of the membrane. DsbB and VKOR family members use an intermediary protein, for example DsbA, rather than interacting directly with substrates. However, some examples exist where the two components (transmembrane protein and intermediary protein) are fused, for example VKOR from Synechococcus sp. Native disulfide bond formation often requires isomerization of disulfide bonds and this is catalysed by a disulfide isomerase, for example DsbC. Both DsbA and DsbC are targeted to the periplasm by an N-terminal signal sequence. In the periplasm DsbC requires the action of the transmembrane protein DsbD which has its active site located on the periplasmic side of the membrane.

While native E. coli disulfide bond containing proteins fold efficiently in the periplasm, the yields of heterologously expressed proteins are often very low, in part due to the small size of the periplasm. In addition, the outer membrane of E. coli is freely diffusible to most small molecules which means that the biophysical environment of the periplasm is dependent on the external media.

EP 0 992 588 A1 describes bacterial expression plasmids encoding DsbA, DsbB, DsbC and DsbD in addition to the heterologous protein to be produced in the bacterial cell. The expression plasmid enables expression of active heterologous protein in both periplasmic and spheroplast fraction, but not in the cytoplasm.

II. Disulfide bond formation in the cytoplasm of modified E. coli. E. coli has two pathways to ensure that its cytoplasm is reducing: i) using thioredoxins/thioredoxin reductases and ii) using glutathione/glutaredoxin/glutathione reductase. When both pathways are knocked out, for example in the commercial Rosetta-Gami™ (Novagen) or SHuffle® (New England Biolabs) strains, the cytoplasm is less reducing and disulfide bonds form in proteins. However, there is no active oxidase in the system and so disulfide bond formation is still slow and inefficient and dependent on external factors. In addition, these strains grow significantly more slowly than wild type strains. While some disulfide bond containing proteins can be formed in the cytoplasm of Rosettagami, or equivalent strains, the yields of many proteins are often below that required for commercial production.

Since the prior art routes for producing disulfide bonded proteins in prokaryotes have various drawbacks, there is a need for improved systems for the production of desired disulfide bonded proteins in prokaryotic hosts, in particular in bacterial hosts.

SUMMARY

One object of the present invention is to provide a method for producing protein(s) of interest containing one or more disulfide bonds in their native state in a prokaryotic host.

Another object of the present invention is to provide a prokaryotic host cell for producing protein(s) of interest containing one or more disulfide bonds in their native state.

Still another object of the invention is to provide a vector system which can be used in introducing into and/or expressing desired genes in said prokaryotic hosts.

To achieve these objects the invention is characterized by the features that are enlisted in the independent claims. Other claims represent the preferred embodiments of the invention.

There exist at least two pathways to ensure that disulfide bond formation in proteins in the cytoplasm is minimal: (i) the glutathione/glutathione reductase pathway and (ii) the thioredoxin/thioredoxin pathway. Due to these cytoplasmic pathways, and the lack of existence of pathways to catalyse cytoplasmic disulfide bond formation, non-regulatory disulfide bond formation in bacteria is restricted to the periplasmic space.

It has now been surprisingly found that the use of expression of inverted DsbB (iDsbB) or inverted VKOR (iVKOR) in prokaryotes, generates disulfide bonds in folding proteins in the cytoplasm. Equally surprisingly after engineering inversion of one DsbB, some naturally occurring inverted VKOR family members were identified.

DsbB and VKOR catalyse the reaction:

where the quinone is either ubiquinone (aerobic conditions) or menaquinone (anaerobic conditions) for DsbB and is thought to be a form of vitamin K for VKOR. Since DsbB is specific for the oxidation of DsbA, cytoplasmic expression of DsbA is required along with iDsbB to allow for disulfide bond formation in cytoplasmically expressed proteins. Typically VKOR family members also require the use of an intermediary protein. For example the active site of VKOR or iVKOR as disclosed herein also requires expression of DsbA or a corresponding protein capable of providing electrons to the active site(s) of VKOR or iVKOR in order to function efficiently. Some VKOR family members are formed from a fusion of the VKOR domain and the intermediary protein.

By inverting the topology of DsbB (iDsbB) such that the cysteines of the active site(s) are now cytoplasmically localised, it is possible for iDsbB to accept electrons directly from a cytoplasmically expressed version of DsbA (cDsbA). This would allow reconstruction of the natural pathway for disulfide bond formation pathway not in the periplasm but in the cytoplasm of prokaryotes. Inversion is needed also if a VKOR species is used not having the cysteines of the active site(s) cytoplasmically localised. In a similar manner VKOR or iVKOR requires expression of DsbA or a corresponding protein capable of providing electrons to the active site(s) of VKOR or iVKOR.

In one aspect the present invention provides a method for producing disulfide bond containing proteins in prokaryotic cells, which comprises the steps of
  expressing in the cytoplasm of a prokaryotic cell
  protein(s) of interest that naturally contain disulfide bonds,
  naturally occurring or inverted transmembrane enzyme, wherein the cysteines of the active site(s) are naturally or after genetic engineering located towards the prokaryotic cytoplasm and said enzyme is capable of catalysing the process of native disulfide bond formation, said enzyme being selected from the group of VKOR, inverted VKOR (iVKOR) and inverted DsbB (iDsbB), and
  cytoplasmic DsbA or a corresponding protein being capable of providing electrons to the active site(s) of VKOR, iVKOR or iDsbB
  whereby natively folded disulfide bond containing protein(s) of interest are formed in the prokaryotic cytoplasm.

As disclosed herein the orientation of the transmembrane enzyme VKOR, iVKOR or iDsbB depends on the charge distribution of the said enzyme in the membrane.

In an embodiment of the invention the removal or addition of one or more lysine and/or arginine residues changes the charge distribution of the enzyme VKOR, iVKOR or iDsbB across the membrane.

The change of orientation of the transmembrane enzymes is typically done using genetic engineering methods. In an embodiment genetic engineering of said DsbB or VKOR comprises the following steps of
  removing one or more of the cytoplasmic lysine and/or arginine residues of DsbB or VKOR, and/or
  fusing DsbB or VKOR to a transmembrane helix or transmembrane helices of any transmembrane protein,
  whereby the charge distribution of the said enzyme in the membrane is changed and the said active site(s) of said DsbB or VKOR protein is shifted towards the prokaryotic cytoplasm.

In an embodiment one or more cytoplasmic lysine and/or arginine residues are removed by mutagenesis or deletion of the N- and/or C-terminus of the DsbB or VKOR protein.

In an embodiment the prokaryote is a bacterium, preferably a Gram negative bacterium, such as E. coli.

In another aspect the present invention provides a prokaryotic host cell genetically engineered to express
  transmembrane enzyme selected from the group of VKOR, inverted VKOR (iVKOR) and inverted DsbB (iDsbB) catalysing the process of native disulfide bond formation and having the cysteines of the active site naturally or after genetic engineering located towards the prokaryotic cytoplasm, and
  cytoplasmic DsbA or a corresponding protein being capable of providing electrons to the active site(s) of VKOR, iVKOR or iDsbB,
  said host cell being capable of forming natively folded disulfide bond containing protein(s) of interest in the cytoplasm.

In an embodiment the method or host cell further comprises expressing in the cytoplasm of a prokaryotic host cell a thiol-disulfide isomerase, such as DsbC or PDI.

In an embodiment a nucleic acid sequence encoding transmembrane enzyme VKOR or inverted VKOR (iVKOR) or inverted DsbB (iDsbB) is chromosomally integrated or is in a vector.

In an embodiment a nucleic acid sequence encoding DsbA or a corresponding protein being capable of providing electrons to the active site(s) of VKOR, iVKOR or iDsbB, or a nucleic acid sequence encoding a thiol-disulfide isomerase, such as DsbC or PDI, is chromosomally integrated or is in a vector.

In another aspect the present invention provides a method for producing a prokaryotic host cell for producing disulfide bond containing protein(s) of interest.

In still another aspect the present invention provides a vector system, which comprises
  a vector encoding VKOR, iVKOR and/or iDsbB and cytoplasmic DsbA or a corresponding protein being capable of providing electrons to the active site(s) of VKOR, iVKOR or iDsbB, and optionally a site for a nucleic acid sequence encoding protein(s) of interest, or
  a first vector encoding VKOR, iVKOR and/or iDsbB, and a second vector encoding cytoplasmic DsbA or a corresponding protein being capable of providing electrons to the active site(s) of VKOR, iVKOR or iDsbB,
  said first or said second vector optionally having a site for a nucleic acid sequence encoding protein(s) of interest.

In an embodiment the vector system further comprises that one of the vectors encodes cytoplasmic thiol-disulfide isomerase, such as DsbC or PDI.

The advantage of the present invention is that the protein of interest is formed in soluble form. Typically no denaturation and renaturation steps of the protein are needed. Furthermore, the protein is produced directly in biologically active form. Compared to prokaryotic hosts used in the prior art, such as E. coli the prokaryotic hosts as described herein are capable of producing even 100× times higher level of desired proteins in an active form.

Panel A: Expression of cPhoA+/−cDsbA from T7 promoter of pET23 with or without pre-expression of $H_0DsbB^{1/9b}$ from an arabinose promoter in pLysSBAD. For these experiments induction of $H_0DsbB^{1/9b}$ was with 0.5% arabinose. Neither cDsbA nor inverted DsbB are able by themselves to increase the yield of active cPhoA.

Panel B: Expression of cPhoA+cDsbA from an arabinose promoter in pLysS-BAD (induction with 0.5% arabinose) with pre-induction of wild type DsbB, $H_0DsbB^{1/9b}$ or the active site mutant $H_0DsbB^{1/9b}$ C46A from the T7 promoter of pET23 using 10 μM IPTG. Neither pre-expression of wild-type DsbB nor the active site mutant of $H_0DsbB^{1/9b}$ results in the gain of significant cPhoA activity while pre-expression of $H_0DsbB^{1/9b}$ does.

Note: The strain, plasmids and expression conditions used here are different than in FIGS. 4, 6, 8 and 9, to ensure that the results can be generally applied, hence the difference in maximal exogenous cPhoA activity.

Figure 3:
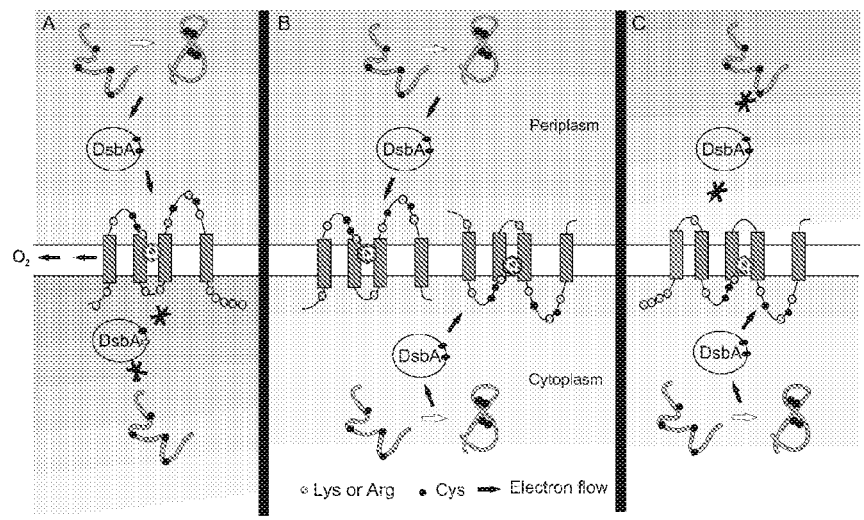

FIG. 3. Original and engineered membrane topology of DsbB. (A) The active site cysteines (black circles) of wild-type DsbB are periplasmic. Electrons (black arrows) flow from folding proteins in the periplasm to DsbA, then to DsbB, then to quinones. (B) Reducing the number of lysine and arginine residues (light grey circles) that are naturally on the cytoplasmic side of DsbB induces partial topology inversion so that it can catalyse disulfide bond formation in the periplasm and the cytoplasm providing DsbA is expressed in both compartments. (C) Addition of an N-terminal TMH (transmembrane helix) fusion to the DsbB mutants allows oxidative folding to occur only in the cytoplasm.

Figure 4:
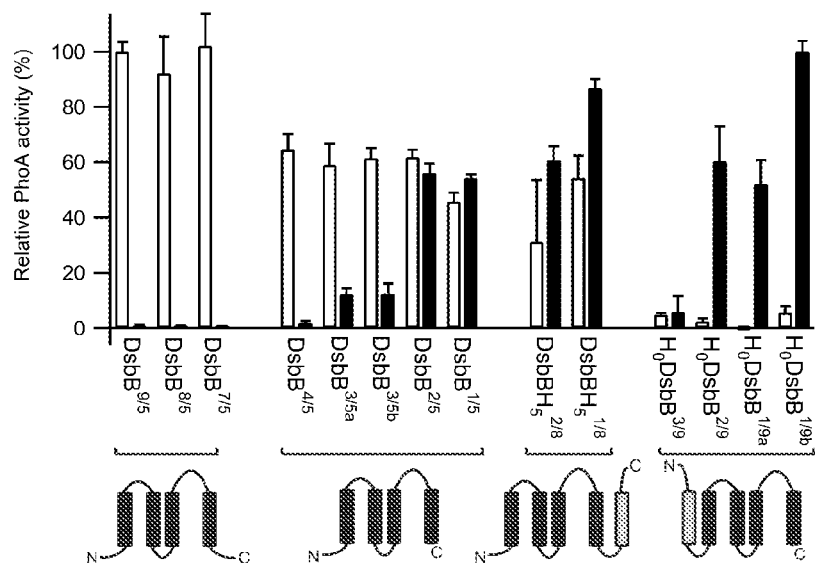

FIG. 4. The activity of DsbB can be inverted across the membrane. DsbB mutants were expressed under a pBAD promoter in the ΔdsbB strain FSH8. The periplasmic activity of DsbB mutants was determined by measuring the activity of pPhoA (white bars) after growth in low-phosphate minimal media while the cytoplasmic activity was determined by expressing cPhoA and cDsbA under a lac promoter in LB media and measuring cPhoA activity (black bars). High pPhoA and cPhoA activities indicate dual topology of the $DsbB^{2/5}$ and $DsbB^{1/5}$ mutants. N-terminal fusion of the first TMH, $H_0(N_{in})$ of MalF (M1-G38), to these mutants results in inverted topology, while C-terminal fusions of the last TMH, $H5(C_{in})$ of MalF (G478-D515) do not. Data represents mean relative activity (%)±sd (n=4). The maximal endogenous pPhoA activity was $\Delta A_{410}$=27.0 mAU/min, the maximal exogenous cPhoA activity was $\Delta A_{410}$=75.6 mAU/min. The cPhoA and pPhoA activities from the negative control, the vector without DsbB, have been subtracted.

Figure 5:
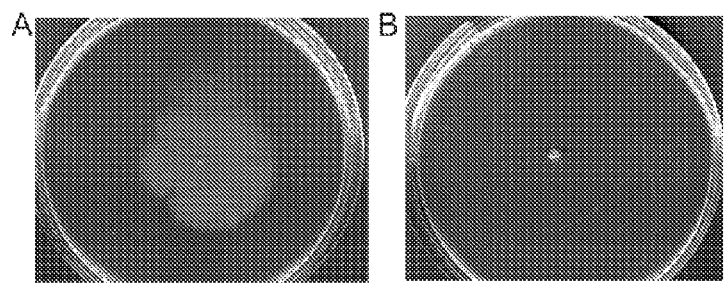

FIG. 5. $H_0DsbB^{1/9b}$ expression does not restore ΔdsbB motility. Motility halos of *E. coli* strain JW5182 harboring a plasmid encoding A) wt DsbB ($DsbB^{9/5}$) and B) $H_0DsbB^{1/9b}$ were examined after 48 hours growth at 30° C.

Figure 6:
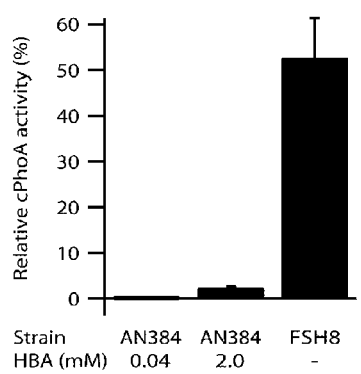

FIG. 6. Efficient oxidative folding in the cytoplasm catalyzed by $H_0DsbB^{1/9a}$ requires an efficient electron transport chain. cPhoA activity was determined in the *E. coli* strain AN384 (ΔubiA ΔmenA) with 0.04 mM or 2 mM quinone precursor hydroxybenzoic acid (HBA) or in the ΔdsbB strain FSH8. Data represents mean relative activity (%) to the maximal exogenous cPhoA activity ($\Delta A_{410}$=75.6 mAU/min)±sd (n=4). The cPhoA activity from the negative control, the vector without DsbB, has been subtracted.

Figure 7:
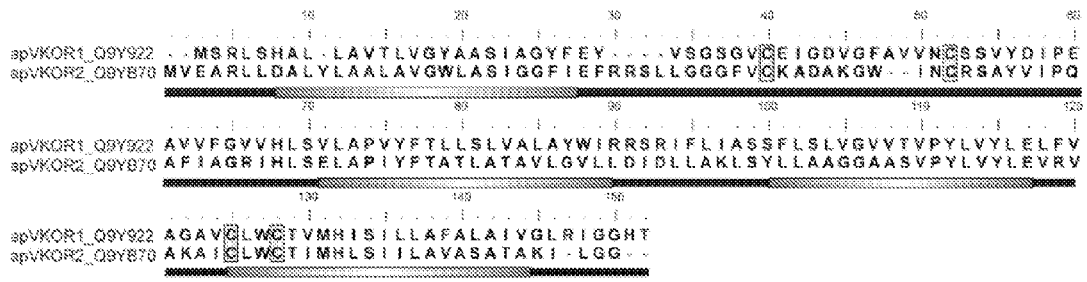

FIG. 7. Sequence alignment of apVKOR1 and apVKOR2. Grey bars represent the four putative transmembrane regions shared by both proteins.

Figure 8:
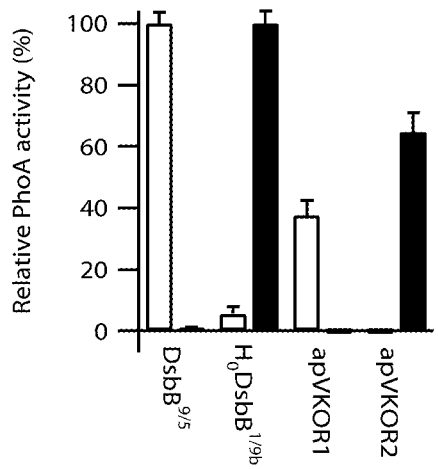

FIG. 8. *A. pernix* has two copies of VKOR that are have different topologies. When expressed in the ΔdsbB *E. coli* strain FSH8 under the pBAD promoter, apVKOR1 and apVKOR2 can catalyse periplasmic and cytoplasmic disulfide bond formation, respectively as determined by the activities of pPhoA (white bars) and cPhoA (black bars). Data represents mean relative activity (%) to the maximal endogenous pPhoA ($\Delta A_{410}$=27.0 mAU/min) or exogenous cPhoA ($\Delta A_{410}$=75.6 mAU/min) activity±sd (n=4). The cPhoA and pPhoA activities from the negative control, the vector without DsbB or VKOR, have been subtracted.

Figure 9:
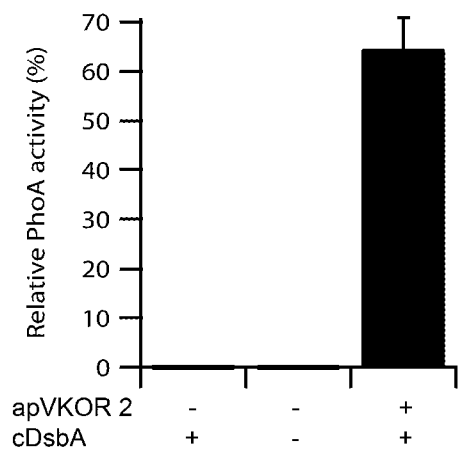

FIG. 9. apVKOR2 dependence on cDsbA. Cells harboring vectors encoding cPhoA or cPhoA+ cDsbA were cotransformed with empty vector or with apVKOR2. After induction cPhoA activity was measured. Data represents mean relative activity (%) to the maximal exogenous cPhoA ($\Delta A_{410}$=75.6 mAU/min) activity±sd (n=4). The cPhoA activity from the negative control, the vector without VKOR, has been subtracted.

Figure 10:
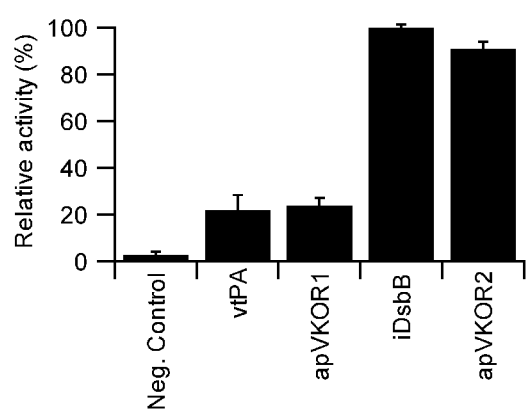

FIG. 10. Inverted DsbB and naturally inverted VKOR can catalyse disulfide bond formation in eukaryotic proteins. Activity measurements of exogenous MBP-vtPA in the *E. coli* strain origami. Data represents the mean relative activity (%) to the maximal exogenous vtPA activity for these data sets ($\Delta A_{405}$=7.9 mAU/min). All samples, except the negative control (Neg), have a polycistronic vector expressing MBP-vtPA+DsbA+DsbC under IPTG induction. apVKOR1, apVKOR2 and $H_0DsbB^{1/9b}$ (iDsbB, inverted DsbB) are pre-expressed under the pBAD promoter from a modified version of pLysS. apVKOR1 is a VKOR i.e. not inverted, apVKOR2 is a naturally occurring inverted VKOR.

DETAILED DESCRIPTION OF THE INVENTION

Definitions

By "transmembrane proteins" are meant proteins in which the polypeptide chain is exposed on both sides of the membrane.

"Dsb" means disulfide bond forming enzymes. Dsb's are enzymes which catalyse thiol-disulfide exchange reactions in the periplasm of prokaryotes. DsbA, DsbC and DsbG belong to the thioredoxin superfamily and are soluble proteins. DsbB and DsbD are transmembrane proteins.

"DsbA" is a soluble periplasmic enzyme, a direct donor of disulfides (acceptor of electrons) when disulfide bonds are being formed in the bacterial periplasm.

"DsbB" is a protein that oxidizes the periplasmic protein DsbA, which in turn oxidizes cysteines in other periplasmic proteins in order to make disulfide bonds. DsbB is a transmembrane protein. There are four catalytic cysteines in DsbB, which are necessary for it to function properly in vivo. DsbB spans the membrane four times and both N-terminus and C-terminus are located in the cytoplasm. Both periplasmic loops of DsbB have two essential catalytic cysteines. DsbB may contain additional non-catalytic cysteines.

"VKOR" is vitamin-K dependent oxidoreductase. VKOR family members are found in bacteria, archaea and eukaryotes. VKOR is a transmembrane protein. VKOR family members include proteins in which VKOR is genetically fused to one or more other proteins. As such VKOR family members exhibit variable numbers of transmembrane regions, but the core VKOR domain usually spans the membrane four times. The two non-cytoplasmic loops in the core VKOR domain are located in the periplasm in bacteria and in the endoplasmic reticulum lumen in eukaryotes and each contain two active site cysteines. In some fusion forms the number of catalytic cysteines may be higher. VKOR may contain additional non-catalytic cysteines.

"Inverting" means altering the membrane topology of a transmembrane protein such that some or all parts of the protein has a reversed topology. More specifically it means that the charge distribution of a transmembrane protein, here in particular DsbB or VKOR, is changed across the membrane and the said active site(s) of said enzyme(s) is/are shifted towards the cytoplasm, in Gram-negative bacteria from periplasmic space towards the cytoplasm.

"iDsbB" means an inverted form of protein DsbB with the active site(s) towards the cytoplasm.

"iVKOR" means an inverted form of VKOR with the active site(s) towards the cytoplasm.

"Active site(s)" means the one or more site(s) on the surface of the enzyme molecule that has just the right shape and functional groups to bind to at least one of the reacting molecules and to catalyse the reaction.

The active site(s) of DsbB or VKOR includes cysteines. As disclosed herein for example the active site(s) of VKOR, iVKOR or iDsbB comprise(s) at least four cysteines located towards the prokaryotic cytoplasm.

"Charge distribution" means the distribution of amino acids with charged side chains in a transmembrane protein across the membrane. In particular, the distribution of amino acids with positively charged side chains (lysine, arginine and to a lesser extent histidine).

When inverting a transmembrane enzyme DsbB or VKOR by genetic engineering methods, a fusion step of said transmembrane enzyme to a transmembrane helix (TMH) or transmembrane helices (TMHs) of a transmembrane protein may be needed. Any transmembrane protein or transmembrane helix can be used in the fusion construct. Examples of transmembrane proteins are "MalF" and "Leader peptidase Lep". The use of MalF has been exemplified in the examples.

"MalF" means an E. coli membrane protein which is part of the Maltose operon and acts as a maltose transporter subunit. The first transmembrane segment has been previously used to stabilize and reserve the native topology of a fragment of the E. coli protein DsbD. It has also been previously used to generate protein fusions in order to tether proteins to the periplasmic space of the inner membrane of E. coli and to study protein transport across the membrane.

"Leader peptidase Lep" means an E. coli membrane protein, which catalyses the cleavage of signal sequences in the periplasm of E. coli.

"Genetical engineering methods" mean the process by which the genetic information of an organism is changed in a stable manner. This can be made experimentally by the use of for example molecular biological techniques, chemicals or radiation. The term mutagenesis is here used as a synonym for genetical engineering.

"Cytoplasmically targeted" means something that is located in the cytoplasm.

Thioredoxin superfamily members are for example thioredoxins, protein disulfide isomerases (PDI's) and disulfide bond forming enzymes (Dsb's).

Herein, by "disulfide bond containing proteins" are meant in particular proteins produced recombinantly in a prokaryotic host. The proteins contain one or more disulfide bonds in their native state which are required to attain their native conformation. Many such proteins when expressed in a system in which disulfide bond formation is limited form insoluble inclusion bodies within the host.

Herein, by "protein of interest" is meant proteins that contain (comprise) one or more disulfide bonds in their native state which are required to attain their native conformation. Many such proteins when expressed in a system in which disulfide bond formation is limited form insoluble inclusion bodies within the host. A protein of interest is here typically a eukaryotic protein, usually a mammalian protein, in particular a human protein. The method of the present invention has been exemplified by producing E. coli alkaline phosphatase and a fragment of human tissue plasminogen activator (vtPA).

The protein may have in its native state multiple disulfide bonds. The method of the present invention is particularly suitable for producing a protein having in its native state two or more disulfide bonds.

Compared to prokaryotic hosts used in the prior art, such as E. coli, the prokaryotic hosts as described herein are capable of producing proteins of interest at least 4× times, typically at least 10× times, preferably at least 15× times, more preferably at least 50× times, still more preferably at least 50× times higher level of desired proteins in an active form.

The term "a prokaryote" has here its ordinary meaning comprising bacteria and archaea.

By "a host" is meant here in particular a prokaryotic host. More specifically the host can be a bacterial host, in particular a gram negative host, such as Escherichia coli (E. coli). In one preferred embodiment the host is E. coli.

According to this disclosure it is possible to produce a natively folded disulfide bond containing protein in a prokaryotic host. According to a preferred embodiment of the invention the protein may be recovered and optionally purified from the cultured host cells. The protein may be lyophilized or formulated with a carrier or diluents, if needed.

The advantage of the present invention is that the protein of interest is produced directly in a biologically active form. Typically no denaturation and renaturation steps of the protein are needed. Commercially significant proteins which may be produced by using the present invention comprise for example insulin, blood coagulation factors, cytokines, chemokines, interferons, growth hormones and single chain antibodies and many others.

In the disclosure the "biological activity" of a protein is deduced by well known methods in the art appropriate for the individual proteins being assayed. The biological activity or function of a protein reflects characteristics of the protein that result from the structure and conformational flexibility of the protein. These in turn are often dependent on the formation of native disulfide bonds. Hence biological activity, for example the ability of an enzyme to catalyze a specific enzymatic activity, is a measure of the attainment of the formation of native disulfide bonds within a protein.

The present invention provides a method for the production of proteins that require disulfide bond formation to reach their native biologically active conformation. The methods presented are particularly suitable for the expression of biologically active proteins that require the formation of multiple disulfide bonds. By multiple disulfide bonds is here meant two or more than two disulfide bonds.

"A vector" means a genetic element which is used as a vehicle to transfer typically foreign genetic material into the genome of a host cell.

According to the present disclosure the vector or vectors are constructed to be capable of expressing VKOR, iVKOR or iDsbB and cytoplasmic DsbA or a corresponding protein being capable of providing electrons to the active site(s) of VKOR, iVKOR or iDsbB, and optionally a protein of interest in the cytoplasm of the prokaryotic host cell.

The system may comprise that VKOR, iVKOR or iDsbB are encoded by one vector and cytoplasmic DsbA or a corresponding protein being capable of providing electrons to the active site(s) of VKOR, iVKOR or iDsbB by another vector. The first or the second vector may optionally have a site for a nucleic acid sequence encoding (a) protein of interest(s).

Any of VKOR, iVKOR or iDsbB or cytoplasmic DsbA or a corresponding protein being capable of providing electrons to the active site(s) of VKOR, iVKOR or iDsbB may be chromosomally integrated or in a vector. Also the protein of interest may be chromosomally integrated or in a vector.

The vector system can be introduced to a suitable prokaryotic host cell and the host can be cultured to produce a protein of interest comprising natively folded disulfide bonds.

The vector system furthermore comprises regulatory elements for multiplying and expressing the nucleic acid sequences in a prokaryotic host. The vector system may comprise also selection markers. The vector system may comprise also a system for inducing expression.

Host cells encoding VKOR, iVKOR or iDsbB and cytoplasmic DsbA and a protein of interest are cultured to produce the protein of interest in a biologically active form.

Methods for cloning the genes of interest into appropriate vectors and culturing prokaryotic organisms are well known in the art.

The construction of suitable vectors has been exemplified here in the examples which report the use of pET23 and pLysS plasmid derivatives. These have ampicillin and chloramphenicol selection markers, respectively. T7 and arabinose inducible expression systems were used.

Any suitable culture media may be used for the cultivation of the prokaryotic organisms. In the examples reported here Luria-Bertani Media (LB media) was used.

The protein may be obtained from the cultured cells in a soluble form by routine cell lysis methods.

Cell lysis can be performed for example by the addition of lysozyme to the resuspended cell pellet followed by freeze-thawing.

The protein of interest can be isolated from the cell lysate in substantially pure form by methods well known in the art and that are appropriate for the individual proteins and final application, for example column chromatography, polyacrylamide electrophoresis, or HPLC analysis. This can include the addition of a fusion tag to the protein of interest to aid purification.

Useful purification methods are for example methods where N-terminal hexahistidine (HIS) or N-terminal maltose binding protein (MBP) tags are used to facilitate purification using immobilized metal affinity chromatography or amylose resin, respectively.

"A substantially pure protein" means a preparation which is at least 60% by weight (dry weight) the protein of interest. Preferably the preparation is at least 75%, more preferably at least 80%, still more preferably at least 90%, still more preferably at least 95%, most preferably at least 99% by weight of the protein of interest.

In some applications the protein product comprising the protein of interest may be used with the cell culture without recovery, isolation and/or without purification. In other applications the protein product comprising the protein of interest may be recovered from the cell culture or cell medium or from host cells with or without purification. Furthermore, in some applications the protein product or purified protein may be diluted or concentrated, or lyophilized.

According to a preferred embodiment of the invention the vector or vectors is a plasmid or plasmids.

Disulfide bond formation in the periplasm is catalysed by enzymes belonging to the Dsb and VKOR families. DsbA, the first family discovered, catalyses the co- and post-translational formation of disulfide bonds in secreted and membrane proteins. In order for DsbA to oxidise a protein dithiol to a disulfide, the active site of DsbA must be regenerated by the transmembrane protein DsbB. DsbB uses quinones as a cofactor. The flow of electrons from substrate proteins via DsbA and DsbB terminates with molecular oxygen under aerobic growth or with fumarate (or nitrate) under an aerobic growth. The key enzyme player in this process which links the respiratory chain within the lipid bilayer of the inner membrane to disulfide bond formation is DsbB.

The active site of DsbA, or a corresponding protein being capable of providing electrons to the active site(s) of iDsbB, VKOR or iVKOR after oxidizing a dithiol to a disulfide in a substrate protein must have its own active site disulfide regenerated by the membrane embedded protein iDsbB, VKOR or iVKOR.

By "a corresponding protein being capable of providing electrons to the active site(s) of VKOR, iVKOR or iDsbB" as cytoplasmic DsbA is here meant a protein which is able to take electrons from a substrate protein during the process of disulfide bond formation in said substrate protein and transfer them to the active site of VKOR, iVKOR or iDSbB. All known proteins with this ability are in the thioredoxin super-family.

Figure 1:
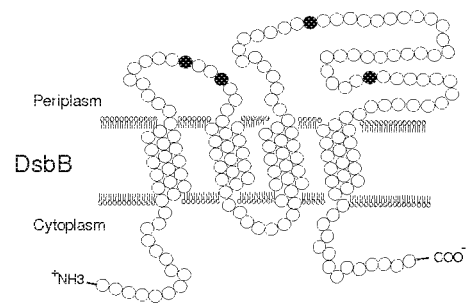
FIG. 1. Schematic of the topology of wild type DsbB (Panel A) and iDsbB (Panel B). The black circles represent the active site cysteine residues. The additional transmembrane region from MalF with the PW linker is shown in shaded circles.
Figure 1B:
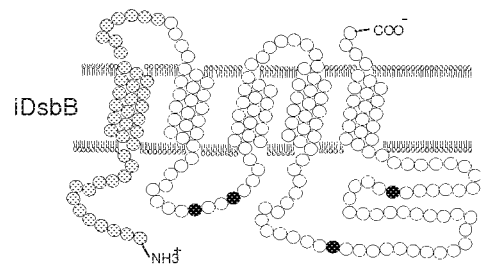

DsbB has four transmembrane segments that form a helical bundle embedded in the membrane (FIG. 1). The four helices are connected by two periplasmic loops, each of which contains two catalytic cysteines, C43/C46 and C106/C132 (numbering for the longer variant of full length $E.\ coli$ DsbB), and by a short cytoplasmic loop. The first active site is close to the periplasmic leaflet of membrane and is oxidised directly by quinones.

There is limited evidence for a function of the cytoplasmic regions of DsbB or for cytoplasmic factors in the function of DsbB. Therefore, in the present invention the idea to invert the topology of DsbB was based on the observations that there is abundance of positively charged residues (K and R) on the cytoplasmic side of the membrane (the so-called "positive inside" rule). The majority of the cytoplasmic lysine and arginine residues were therefore removed, either by mutagenesis and/or by deletion of the N- and C-terminus of the protein. In addition, the truncated N-terminus of DsbB was fused to the first transmembrane helix of the maltose transporter MalF (FIG. 1). Alternatively, the truncated C-terminus of DsbB was fused to the last transmembrane helix of the maltose transporter Mal F.

While MalF was used as an example, DsbB or VKOR or mutants thereof can be fused to a part of any suitable transmembrane protein (natural or artificial) to mediate inversion. It is important that the final construct has inverted DsbB or VKOR topology based on the membrane distribution of positively charged residues (lysine, arginine and to a lesser extent histidine). The membrane proteins are orientated in such a way that positively charged amino acids are found predominantly in the cytoplasm. In the method of the present disclosure this was achieved by the deletion of the positively charged N- and C-terminus of DsbB as well as removing the cytoplasmic lysine and arginine residues by internal mutations. A transmembrane region of MalF was also added as a fusion.

After successfully inverting the topology of $E.\ coli$ DsbB naturally occurring topologically inverted DsbB and VKOR family members were searched for. Using global membrane topology prediction algorithms (SCAMPI) examined 1042

DsbB and 243 prokaryotic and archaeal VKOR family members from Pfam were searched. While no naturally occurring DsbBs with inverted topology were identified, 5 species were found that contain VKOR homologues that are predicted to have cytoplasmic localization of their catalytic sites. All 5 species were hyperthermophiles. It is important that these natural proteins with putative inverted topology were identified using the same membrane distribution of positively charged residues as was used to engineer inversion of DsbB, hence there is no intrinsic difference between naturally inverted proteins and those engineered to have inversion of topology. Subsequently one of these naturally occurring inverted VKOR family members from *Aeropyrum pernix* was shown to have cytoplasmic disulfide bond forming activity.

As is shown below DsbBs and VKORs can be obtained from various sources from prokaryotic as well as from eukaryotic sources or artificial DsbBs or VKORs may be used. The sequences of these transmembrane enzymes may be modified or they may vary naturally in broad range. When inverting these transmembrane enzymes it is essential to ensure an appropriate charge distribution, which means the distribution of amino acids with charged side chains in the transmembrane protein across the membrane. As can be seen below DsbBs may originate from various prokaryotes, typically from bacterial genera, such as *Aeromonas, Azospirillum, Rhodoferax, Burkholderia, Pseudoalteromonas*. VKORs may originate from various prokaryotes, typically from archaeal or bacterial genera, such as *Aeropyrum, Bifidobacterium*, or from eukaryotes, such as human (*Homo sapiens*), or zebrafish (*Danio rerio*). Naturally inverted examples of VKOR are from archaeal genera, such as *Aeropyrum* and *Pyrobaculum*. VKOR examples with fusion partner are from bacterial genera, such as *Synechococcus*, and *Anaeromyxobacter*. Also DsbA may originate from various prokaryotes, typically from bacterial genera, such as *Escherichia*, typically *E. coli*. DsbCs may originate from bacterial genera, such as *Escherichia*, typically *E. coli*.

Examples of DsbBs, VKORs, DsbAs, DsbCs and PDIs:

DsbB Examples (Taken from Various Positions in Full Family Alignment)

```
E. coli DsbB (P0A6M2, long variant AAA23711.1)
                                                        (SEQ ID NO: 1)
MIMLRFLNQCSQGRGAWLLMAFTALALELTALWFQHVMLLKPCVLCIYERCALFGVLGAALIGAIAPKTPLR

YVAMVIWLYSAFRGVQLTYEHTMLQLYPSPFATCDFMVRFPEWLPLDKWVPQVFVASGDCAERQWDFLGLEM

PQWLLGIFIAYLIVAVLVVISQPFKAKKRDLFGR

E. coli DsbB (P0A6M2, short variant AAC23711.1)
                                                        (SEQ ID NO: 2)
MLRFLNQCSQGRGAWLLMAFTALALELTALWFQHVMLLKPCVLCIYERCALFGVLGAALIGAIAPKTPLRYV

AMVIWLYSAFRGVQLTYEHTMLQLYPSPFATCDFMVRFPEWLPLDKWVPQVFVASGDCAERQWDFLGLEMPQ

WLLGIFIAYLIVAVLVVISQPFKAKKRDLFGR

Aeromonas Salmonicida DsbB (A4SN81)
                                                        (SEQ ID NO: 3)
MIEFLRRIAAHRLAWGLLAASALFLELSALFFQYVLGLHPCVMCVYERLAILGVLSAGLLGMVAPEKWYLRW

SALLLWGYSAFRGLQLALKHVDYQMNPSPFNVCSPFADFPSWAPLDQWLPWLFFPDGDCSEISWQFLSFSMP

QWLVAIFAAYLLVFVVVTIGNLVKGRCCS

Azospirillum sp. DsbB (D3NXM8)
                                                        (SEQ ID NO: 4)
MGVADGWPNGSARANLSAMMIQTLLSRVFDDPRIAAPLLALASAGVLLSALFFQFVLGYQPCVLCIMQRWPY

VAVMALGLVTWLFRRWRGVGDALLVVSGLALLAGAGIAAYHVGVEQHWWAGTSSCGGSAPANSLEALRAQVL

AAPVTRCDEVAWSLFGISMAGYNVVISLALAAYAFIAARIAYTRTPVSRTAL

Rhodoferax ferrireducens DsbB (Q21WM5)
                                                        (SEQ ID NO: 5)
MSFQVVTGWLDNSPRRIFAFVSLASIGMLAFGQYLQHVVGLEPCPMCIVQRYALVLVAIIAGLTGASGRKGL

HLGGAVLMLGSSGFGAYVAARQSWLQWYPPEVVSCGRDFYGMITTFPLQRAIPMIFKGSGDCSKVDWTFLGG

SIANWTFVVFGLIVLLSLALIWRRVSRRVS

Burkholderia cenocepacia DsbB (Q1BY52)
                                                        (SEQ ID NO: 6)
MNDYTLALRRERRLLMLLGWVCIALLAGALYLQYVKNEDPCPLCIIQRYFFCAIGIFAFLAAGIRNWRGVWV

LELLIAIAAAGGVGTAARHLSIQMNPGFSCGFDTLQPIVDSLPPAQWFPGMFKVAGLCETVYPPIFGILLPG

WALIGFAVILVAVVASLWRHRRKLAS

Pseudoalteromonas atlantica DsbB (Q15S31)
                                                        (SEQ ID NO: 7)
MTFISNLADTRLAWGLLFLSALVLVAYALFSQHAMGLQPCIMCIYQRTAIFGIMFACVPVLAANNMLTRLFA

FTVWGISAIWGGLIAWEHYDIQNAANPFFATCEIVPNFPSWLPLHEWLPNLFAATGDCGNIDWVFMDMSMPQ

WMMVVFAIYSSIWFVVLASRLIGNRAI
```

VKOR Examples

```
Aeropyrum pernix (Q9Y922)
                                                    (SEQ ID NO: 8)
MSRLSHALLAVTLVGYAASIAGYFEYVSGSGVCEIGDVGFAVVNCSSVYDIPEAVVFGVVHLSVLAPVYFTL

LSLVALAYWIRRSRIFLIASSFLSLVGVVTVPYLVYELFVAGAVCLWCTVMHISILLAFALAIVGLRIGGHT

Bifidobacterium longum (Q8G7Z6)
                                                    (SEQ ID NO: 9)
MTRNTATDTSSSTTNTTPLGLAEARPLIGWRHSATWTYLIMLIASAVALGASLILSAETLQLARHPESALGC

DLNSVVSCSAVAQSWQAEIAKFGGLSYPNAFFGIAAESVFITIAVIGLARVKVPRWFATCTWLGGLAALAYS

YWLSTQSLFVIHALCPWCLTLMFSTTIQFMALSHATVAVQGLPSRKAVAADDSDGEAEVAAVPAGLNKYYRL

NIDLMVDILWIVAIVVLIIVTEGAALFAA

Homo sapiens VKORC1 (Q9BQB6)
                                                    (SEQ ID NO: 10)
MGSTWGSPGWVRLALCLTGLVLSLYALHVKAARARDRDYRALCDVGTAISCSRVFSSRWGRGFGLVEHVLGQ

DSILNQSNSIFGCIFYTLQLLLGCLRTRWASVLMLLSSLVSLAGSVYLAWILFFVLYDFCIVCITTYAINVS

LMWLSFRKVQEPQGKAKRH

Danio rerio vkorc1l1 (Q502B2)
                                                    (SEQ ID NO: 11)
MAAPVLRVSTPRWERIVRLLVCLSGILLSLYSFHVEREKTRDANYRAMCDLSSSISCKVFTSRWGRGFGLL

GSIFGNDSAVNQPNSVYGIFFYVFQLLLGLTASAMAALILMTTSIASVMGSLYLGYILYFVLKDFCVICITT

YALNFILFVLNYKRLVYLNEAWKQQLQAKRD
```

VKOR Examples with Fusion of Partner that Plays Role of DsbA

```
Synechococcus sp VKOR (Q0I736)
                                                    (SEQ ID NO: 12)
MATQRLTSRRRQDQGSKWVRIVMAVLATVGVIDTGSITLKFWGVLGDLTCPMGAGGCDKVLNSPWGTLFQGD

GFSIPLSFSGLIAYLAVLVMAVVPLLPGLSENKADLSRRTWWGLFTVSLVMAVFSLVLVGLMVIKIQAFCFF

CVLSAVLSLTLLVLSLAGGGWDDPSQLLFRGFLLALAVLLGGLIWASVLDPARPDAVATGPGAPPPVLTESN

PAKISLAEHLTASGAVMYSAYWCPHCHEQKEMFGQEAAKTLKVVECAPTGQNNEAKLCQSKGIEGFPTWEIN

GELDSGVKKLPELARLSGYQGSKDF

Anaeromyxobacter sp. VKOR (A7HF26)
                                                    (SEQ ID NO: 13)
MTRDRKKKPDRRPSAPTPAPPRAALLVASLLLALGGVALSVALARLHARAHAGLSSFCAINDVVNCDRVALS

RFSTFLGLPVALWGALGYGLAAVLAARALAHARRGVTAARGLLFAVAAVAVAASAALAVVSELAIGAWCLLC

MASWATAAGLLATAWRACPSGPAAAVAADVAVLRARPARTAALALVALVAVVGARAAYARYAATVPRAPAAS

AGARAPGPISPAPVAAGGVVVEFSDYECPFCARAHEQLATLRAARPDLEIVRRHFPLDAACNPALARSIHPS

ACALARAAICAEAQGRFAEMDDALFRNQQAREPASRLAARLGLDVAAFEACLASPATEARLARDVEDGMRAG

VRATPSYVVGGKVYAGELPPGLLAAPAAPAPPPRAAER
```

Naturally Inverted VKOR Examples:

```
Aeropryum pernix (Q9YB70)
                                                    (SEQ ID NO: 14)
MVEARLLDALYLAALAVGWLASIGGFIEFRRSLLGGGFVCKADAKGWINCRSAYVIPQAFIAGRIHLSELAP

IYFTATLATAVLGVLLDIDLLAKLSYLLAAGGAASVPYLVYLEVRVAKAICLWCTIMHLSIILAVASATAKI

LGG
```

-continued

Pyrobaculum aerophilum (Q8ZXF9)
(SEQ ID NO: 15)
MALYILTGLLAALGVAVGLLGSRLIALSLLAAAGLLHTLFNKPSAFCAKYKIGGCEAVLSSPYARPFGIPLE

YLGAAWFAGVPIAYYLGIGLVWSVMAFAGVIALVAIEAKLRAFCIYCTVAHVIGLAAAFLLL

DsbA Sequence Example

E. coli mature DsbA (DsbA without the signal sequence which will be
cytoplasmically expressed)
Residues 20-208 of P0AEG4 with an initiating Met added
(SEQ ID NO: 16)
(M)AQYEDGKQYTTLEKPVAGAPQVLEFFSFFCPHCYQFEEVLHISDNVKKKLPEGVKMTKYHVNFMGGDLG

KDLTQAWAVAMALGVEDKVTVPLFEGVQKTQTIRSASDIRDVFINAGIKGEEYDAAWNSFVVKSLVAQQEKA

AADVQLRGVPAMFVNGKYQLNPQGMDTSNMDVFVQQYADTVKYLSEKK

DsbC Sequence Example

E. coli mature DsbC (DsbC without the signal sequence which will be
cytoplasmically expressed)
Residues 21-236 of P0AEG6 with an initiating Met added
(SEQ ID NO: 17)
(M)DDAAIQQTLAKMGIKSSDIQPAPVAGMKTVLTNSGVLYITDDGKHIIQGPMYDVSGTAPVNVTNKMLLK

QLNALEKEMIVYKAPQEKHVITVFTDITCGYCHKLHEQMADYNALGITVRYLAFPRQGLDSDAEKEMKAIWC

AKDKNKAFDDVMAGKSVAPASCDVDIADHYALGVQLGVSGTPAVVLSNGTLVPGYQPPKEMKEFLDEHQKMT

SGK

PDI Sequence Example

Human mature PDI (PDI without the signal sequence which will be
cytoplasmically expressed)
Residues 18-508 of P07237 with an initiating Met added
(SEQ ID NO: 18)
(M)DAPEEEDHVLVLRKSNFAEALAAHKYLLVEFYAPWCGHCKALAPEYAKAAGKLKAEGSEIRLAKVDATE

ESDLAQQYGVRGYPTIKFFRNGDTASPKEYTAGREADDIVNWLKKRTGPAATTLPDGAAAESLVESSEVAVI

GFFKDVESDSAKQFLQAAEAIDDIPFGITSNSDVFSKYQLDKDGVVLFKKFDEGRNNFEGEVTKENLLDFIK

HNQLPLVIEFTEQTAPKIFGGEIKTHILLFLPKSVSDYDGKLSNFKTAAESFKGKILFIFIDSDHTDNQRIL

EFFGLKKEECPAVRLITLEEEMTKYKPESEELTAERITEFCHRFLEGKIKPHLMSQELPEDWDKQPVKVLVG

KNFEDVAFDEKKNVFVEFYAPWCGHCKQLAPIWDKLGETYKDHENIVIAKMDSTANEVEAVKVHSFPTLKFF

PASADRTVIDYNGERTLDGFKKFLESGGQDGAGDDDDLEDLEEAEEPDMEEDDDQKAVKDEL

Within the scope of the present invention are also nucleic acid sequences encoding the proteins comprising any of the amino acid sequences of the above gene bank accession numbers or the sequences SEQ ID NO:1 to SEQ ID NO:7 having DsbB activity, or SEQ ID NO: 8 to 15 having VKOR activity or SEQ ID NO: 16 having DsbA activity or SEQ ID NO: 17 having DsbC activity or SEQ ID NO: 18 having PDI activity or nucleic acid sequences encoding a fragment of said sequences or a modified version of said sequences, which sequences still have DsbB or VKOR, or DsbA, or DsbC or PDI activity. Suitable nucleic acid sequences encoding proteins having DsbB or VKOR or DsbA or DsbC or PDI activity are publicly available and can be found in gene banks.

A fragment, modified version (or variant) of an enzyme having DsbB or VKOR activity comprises typically an amino acid sequence having at least 25%, preferably at least 40%, more preferably at least 50%, still more preferably at least 60%, still and still more preferably at least 70%, more and more preferably at least 90% identity, most preferably at least 95% or at least 98% identity to any of the above mentioned amino acid sequences SEQ ID NO: 1 to 7 or 8 to 15, respectively.

By the term "identity" is here meant the identity between two amino acid sequences compared to each other from the first amino acid encoded by the corresponding gene to the last amino acid. Preferably the identity is measured by comparing the amino acid sequences without the sequences of any signal peptide the protein may have. The identity of the full-length sequences may be measured for example by using sequence analysis software, for example BLAST software available from the National Library of Medicine.

The transmembrane enzymes DsbB and VKOR are central to oxidative protein folding in the periplasm of prokaryotes. As described herein the present invention was exemplified by engineering DsbB mutants with inverted membrane topology that catalyze disulfide bond formation in the cytoplasm of *Escherichia coli*. In addition, two naturally occurring and oppositely oriented VKOR homologues from the hyperthermophile *Aeropyrum pernix* were identified that promote oxidative protein folding in the periplasm or cytoplasm respectively.

PhoA used in this disclosure as an example is a protein with two sequential disulfide bonds. For proteins with an increased number of sequential disulfide bonds or with non-sequential disulfide bonds, the formation of the native disulfide state requires the action of a thiol-disulfide isomerase, for example DsbC or PDI. Hence for these more complicated proteins cytoplasmically targeted DsbC (cDsbC) or cytoplasmically targeted protein disulfide isomerase (cPDI) is required. *E. coli* sequences for DsbC (EC 5.3.4.1) can be found for example as Genbank accession numbers AAA83074 or AAC75931 and sequences for PDI (EC 5.3.4.1) comprise for example human PDI or yeast Pdi1p sequences. Yeast Pdi1p sequences can be found for example as Genbank accession numbers CAA42373 or BAA00723 or CAA38402. Human PDI family members are for example PDI Genbank accession numbers CAA28775 or AAC13652.

cDsbA is needed for iDsbB or VKOR or iVKOR to work properly and cytoplasmic DsbC (cDsbC) is needed to sequentially catalyze isomerisation for certain substrate proteins. Both cDsbA and cDsbC as well as cPDI are made cytoplasmic by expressing them without their N-terminal signal sequences.

Sequences for DsbA can be found for example as Genbank accession numbers CAA56736 or AAA23715.

Tissue plasminogen activator (tPA) is a protease that converts plasminogen to plasmin, the major enzyme involved in the breakdown of blood clots. It is used medically to treat pulmonary embolism, myocardial infarction and stroke. It is a large protein that contains 16 non-sequential and one sequential disulfide bond and in addition has one free thiol group in the native structure. It is available under the names Activase and Retavase. Retavase is a fragment of tPA which only contains the kringle 2 and protease domains. A similar fragment of tPA is known as vtPA and has been by academic researchers to study disulfide bond formation. Both Retavase and vtPA contain only 9 disulfide bonds.

iDsbB was constructed by mutagenesis from DsbB. DsbB was truncated from both N and C terminus to exclude the topogenic sequences to give tDB (R14-F168). Then $H_0(N_{in})$ of MalF was fused to the N terminus of tDB.

$H_0(N_{in})$ of MalF is the first transmembrane helix and part of the subsequent periplasmic loop of MalF (M1-G38).

Two additional residues (K68 and R72) located in the cytoplasmic loop of DsbB were mutated to N.

Alkaline phosphatase (pPhoA, where p indicates periplasmic) has two disulfide bonds that are essential for its phosphatase activity Hence, endogenous pPhoA exhibits low activity ($\Delta A_{410}$=1.8 mAU/min) when expressed in a $\Delta$dsbB strain, with a circa 15-fold increase in active pPhoA ($\Delta A_{410}$=27 mAU/min) upon co-expression of wild-type DsbB (see tables 1 and 2 for strains and plasmids used in the examples). Similarly, expression of alkaline phosphatase devoid of its periplasmic targeting sequence (denoted cPhoA for cytoplasmic PhoA), does not result in the production of active protein in the reducing environment of the cytoplasm, unless an active catalyst of de novo disulfide bond formation is present. The inventors reasoned that pPhoA and cPhoA can be used as reporters for periplasmically or cytoplasmically localized disulfide bond forming activity of DsbB or iDsbB respectively as long as DsbA or a corresponding protein being capable of providing electrons to DsbB or iDsbB was present in the appropriate compartment to mediate electron transfer.

In this disclosure the inversion of topology of DsbB was based on the reduction of the number of lysine and arginine residues that normally reside in the cytoplasm (FIG. 1). Wild-type DsbB has 9 (K+R) in the cytoplasm and 5 (K+R) on the same face as the active site in the periplasm (DsbB$^{9/5}$) as well as one R in the middle of transmembrane helix 3. Deletion of the N and C-terminus to truncate DsbB to give tDB (R14-F168) followed by fusion of $H_0(N_{in})$ of MalF and mutation of K68 and R72 located in the cytoplasmic loop of DsbB to N, resulted in the formation of iDsbB.

Figure 2A:
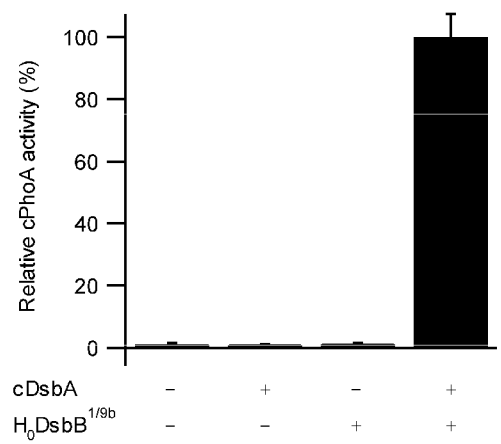
FIG. 2. The activity of inverted DsbB requires expression of cDsbA and active site Cys46. Activity measurements of exogenous cPhoA in the *E. coli* strain BL21(DE3) pLysS. Data represents the mean relative activity (%) to the maximal exogenous cPhoA activity for these data sets ($\Delta A_{410}$=19.5 mAU/min)±sd (n=2).
Figure 2B:
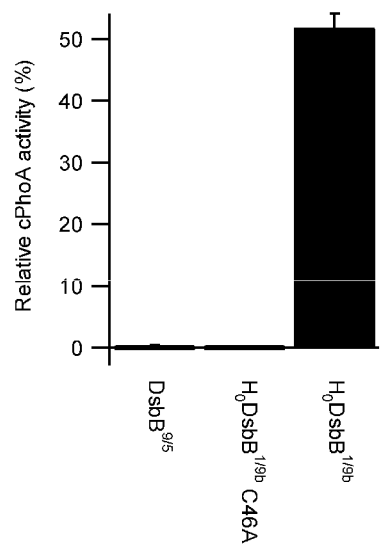

Expression of cPhoA with or without co-expression of cDsbA from the T7 promoter of pET23 results in the formation of negligible amounts of active cPhoA in *E. coli* strain BL21 (DE3) pLysS (FIG. 2A). Similarly when iDsbB is pre-expressed from an arabinose promoter in a modified version of pLysS no active cPhoA is seen unless cDsbA is also expressed. Expression of both iDsbB and cDsbA results in a 100-fold increase in cPhoA activity (FIG. 2A). This represents the formation of the two disulfide bonds in PhoA which are essential for activity. iDsbB expression cannot be replaced by DsbB expression and the C46 active site cysteine is required for iDsbB activity (FIG. 2B).

There are multiple possible ways to invert DsbB, all of which depend on altering the charge distribution of the protein. In addition to inversion, the topology of a transmembrane protein maybe partially inverted or mixed topology, resulting in activity on both sides of the membrane such that both active pPhoA and cPhoA can be produced (FIG. 3). This can be observed by the systematic reduction of the number of lysine and arginine DsbB residues that normally reside in the cytoplasm.

Point mutations K68Q (DsbB$^{8/5}$) or K68Q/R72N (DsbB$^{7/5}$) removing one or two of the cytoplasmic charges, results in no change in cPhoA or pPhoA activity (FIG. 4). In contrast, deletion of the C-terminus of DsbB ($\Delta$K169-R178) combined with the point mutation R5N (DsbB$^{3/5a}$) or K68Q (DsbB$^{3/5b}$) results in the removal of 6 (K+R) residues from the side opposite to the active site and conferred low but significant cPhoA activity (FIG. 4), corresponding with a partial topology inversion of these mutant DsbBs. Combining R5N/K68Q (DsbB$^{2/5}$) or making the R72N substitution in this background (DsbB$^{1/5}$) increased cPhoA activity substantially compared with wild-type DsbB, indicating major topology inversion towards the cytoplasm. The gain of cytoplasmic activity was concomitant with a decrease in periplasmic activity to around 46% of wild-type for DsbB$^{1/5}$. Hence, DsbB$^{2/5}$ and DsbB$^{1/5}$ can simultaneously catalyse oxidative protein folding in two different cellular compartments indicating mixed or dual topology of these mutants.

In order to force DsbB towards a fully inverted topology either the first or the last TMH from *E. coli* maltose transporter MalF was fused to truncated mutated DsbB constructs. A C-terminal fusion of the terminal TMH from MalF, which has 3 (K+R) after the TMH, after F168 of $\Delta$K169-R178 R5N K68Q DsbB (DsbBH$_5^{2/8}$) and the subsequent R72N mutation (DsbBH$_5^{1/8}$) resulted in the formation of active proteins, but had a relatively small effect on shifting the topology towards inversion compared with DsbB$^{2/5}$ or DsbB$^{1/5}$ (FIG. 4). In contrast fusion of the first TMH from MalF, which has 4 (K+R) prior to the TMH, N-terminally to $\Delta$M1-G13 $\Delta$K169-R178 DsbB to give $H_0$DsbB$^{3/9}$ resulted in a protein that displayed low cPhoA and pPhoA activity. However, a single additional mutation, K68Q in L3 ($H_0$DsbB$^{2/9}$) leads to a dramatic increase in cytoplasmic activity (FIG. 4), suggesting topological instability of $H_0$DsbB$^{3/9}$. A further point mutation, R72N giving H$_0$DsbB$^{1/9a}$ showed no detectable pPhoA activity above the vector negative control, but very high cPhoA activity (FIG. 4). A similarly charged species with K68N instead of K68Q (H$_0$DsbB$^{1/9b}$) also showed minimal pPhoA activity, but had increased cPhoA activity, presumably linked to changes in structure. In addition, H$_0$DsbB$^{1/9b}$ did not restore DsbB-dependent motility (FIG. 5), suggesting a complete relocalization of its disulfide forming activity from the periplasm to the cytoplasm i.e. full inversion of topology from DsbB to iDsbB. As a control for non-specific effects, subcellular fractionation of *E. coli* expressing H$_0$DsbB$^{1/9b}$, cDsbA and cPhoA showed that cPhoA is retained mostly in the cytoplasm and that the subcellular localization of internal markers such as β-galactosidase, β-lactamase was not affected (Table 3).

iDsbB shows here the same dependence on DsbA as an intermediary as the wild-type protein does (FIG. 2). To examine whether the inverted DsbB proteins also use quinone one in *E. coli* strain AN384 (ΔubiA420 ΔmenA401) was expressed and tested for cPhoA activity. Consistent with the results for wild-type DsbB H$_0$DsbB$^{1/9a}$ failed to catalyse cytoplasmic disulfide bond formation in AN384 (FIG. 6), indicating that quinone dependence is retained with DsbB inversion. Hence inversion occurs with conservation of activity and specificity.

Disulfide bond formation in bacteria and archaea is catalysed either by DsbB or VKOR. As per DsbB, VKOR family members have multiple transmembrane helices that form a helix-bundle. That DsbB showed topological plasticity and that cytoplasmic disulfide bonds are readily formed once catalysts for their formation are co-localized, suggested that the occurrence of naturally occurring topologically inverted catalysts of disulfide bond formation is evolutionarily plausible. Within the DsbB and VKOR families was systematically searched for members that are predicted to have their catalytic residues in the cytosol. Using global membrane protein topology prediction algorithms (SCAMPI), we examined 1042 DsbB and 243 VKOR bacterial and archaeal homologues we searched from Pfam. While no naturally occurring DsbB members with inverted topology were found, 5 species containing VKOR homologues that are predicted to have cytoplasmic localization of their catalytic sites were identified, all of which belong to the hyperthermophilic crenarchaeon phylum (Table 5). Each of these had two VKOR homologues in their genome, of similar size and number of TMHs (FIG. 7), which are predicted to possess opposite topologies To test the topology prediction, apVKOR1 and apVKOR2 were expressed from the hyperthermophile *Aeropyrum pernix* in *E. coli* and tested for disulfide bond formation in the cytoplasm and the periplasm. Expression of apVKOR1, with predicted normal VKOR topology and the active sites in the periplasm, induced disulfide bond formation only in pPhoA, whereas apVKOR2, with predicted iVKOR topology, induced disulfide bond formation only in cPhoA (FIG. 8), with iVKOR activity being dependent on co-expression of cDsbA (FIG. 9). This indicates that both proteins can catalyse disulfide bond formation and that they have opposite membrane orientation of their active sites. The molecular mechanism by which the two VKOR family members from *Aeropyrum pernix* evolved to attain two distinctly localized disulfide bond formation activities appears to be a gene duplication event followed by the redistribution of positively charged amino acids across the sequence of one copy by loop deletion and mutational substitution (FIG. 7). This is directly analogous to the in vitro methodology used to create iDsbB.

To confirm that the system is not specific for the formation of disulfide bonds in prokaryotic proteins we examined disulfide bond formation in human vtPA. vtPA is a fragment of tissue plasminogen activator which contains 9 disulfide bonds. The activity of the protein is dependent on the formation of native disulfide bonds and requires the presence of an disulfide isomerase as well as catalyst of disulfide bond formation. When we expressed vtPA, tagged to maltose binding protein to increase the solubility of folding intermediates, with cDsbA and cDsbC in the cytoplasm of the *E. coli* strain origami, low activity was obtained. This vtPA activity did not increase when apVKOR1 from *Aeropyrum pernix* was pre-expressed, consistent with its topology having the active site cysteines in the periplasm. However, when apVKOR2 (a naturally inverted VKOR) or iDsbB were pre-expressed a circa 4-5 fold increase in vtPA activity was observed (FIG. 10).

The present disclosure presents the first time that the enzymatic activity, including specificity, of a membrane protein can be totally inverted across the membrane.

The following non-limiting examples illustrate the invention.

EXAMPLES

Example 1

Materials and Methods

Strains:
The *E. coli* strains used in this study are shown in Table 1.

TABLE 1

*E. coli* strains

| Strain | Relevant genotype | Source |
|---|---|---|
| BL21 (DE3) | ompT, λ(DE3) | Novagen |
| BW25113 | Parental strain of Keio collection | Keio collection |
| JW5182 | BW25113 dsbB::KAN | Keio collection |
| FSH8 | JW5182 ara+ | This study |
| AN384 | ubiA420 menA401 | (Wallace et al. 1977) |

Standard P1 transduction was used to construct dsbB:KAN ara+ with selection on M65 salts with 0.2% arabinose as the sole carbon source.

Vectors Constructions:
A list of all of the plasmid vectors used in this study is shown in Table 2.

TABLE 2

Plasmid vectors used in this study. Pictorial representations of the transmembrane proteins are shown in each case with the active site face uppermost and positively charged residues (K + R) indicated by black circles.

| Plasmid | Vector | Encodes | Source | Representation |
|---|---|---|---|---|
| pFH313 | pMALc2x | SpeI site added upstream of rbs | New England Biolabs | |

TABLE 2-continued

Plasmid vectors used in this study. Pictorial representations of the transmembrane proteins are shown in each case with the active site face uppermost and positively charged residues (K + R) indicated by black circles.

| Plasmid | Vector | Encodes | Source | Representation |
| --- | --- | --- | --- | --- |
| pFH368 | pFH313 | MH$_6$M-cPhoA (R22-K271) | This study | |
| pFH314 | pFH313 | MH$_6$M-cPhoA (R22-K271) and MH$_6$M-cDsbA (A20-K208) | This study | |
| pVD80 | pET23a | MH$_6$M-cPhoA (R22-K271) | (Nguyen et al, 2011) | |
| pFH258 | pET23a | MH$_6$M-cPhoA (R22-K271) and MH$_6$M-cDsbA (A20-K208) | This study | |
| pFH273 | pLysSBAD | M-cPhoA (R22-K271) and MH$_6$M-cDsbA (A20-K208) | This study | |
| pFH257 | pLysSBAD | Erv1p (Met1-Glu189) | (Nguyen et al, 2011) | |
| pFH277 | pLysSBAD | Nothing | This study | |
| pFH371 | pLysSBAD | apVKOR1 (Met1-Thr145) | This study | |
| pFH372 | pLysSBAD | apVKOR2 (Met1-Gly147) | This study | |
| pFH186 | pET23 | DsbB$^{9/5}$; DsbB (M1-R178) | This study | |
| pFH315 | pLysSBAD | DsbB$^{9/5}$; DsbB (M1-R178) | This study | |
| pFH316 | pLysSBAD | DsbB$^{8/5}$; DsbB (M1-R178) K68Q | This study | |
| pFH318 | pLysSBAD | DsbB$^{7/5}$; DsbB (M1-R178) K68Q, R72N | This study | |

TABLE 2-continued

Plasmid vectors used in this study. Pictorial representations of the transmembrane proteins are shown in each case with the active site face uppermost and positively charged residues (K + R) indicated by black circles.

| Plasmid | Vector | Encodes | Source | Representation |
|---|---|---|---|---|
| pFH323 | pLysSBAD | DsbB$^{4/5}$; DsbB (M1-F168) | This study | |
| pFH327 | pLysSBAD | DsbB$^{3/5a}$; DsbB (M1-F168) R5N | This study | |
| pFH324 | pLysSBAD | DsbB$^{3/5b}$; DsbB (M1-F168) K68Q | This study | |
| pFH328 | pLysSBAD | DsbB$^{2/5}$; DsbB (M1-F168) R5N, K68Q | This study | |
| pFH330 | pLysSBAD | DsbB$^{1/5}$; DsbB (M1-F168) R5N, K68Q, R72N | This study | |
| pFH357 | pLysSBAD | DsbBH$_5^{2/8}$; DsbB (M1-F168) R5N, K68Q + GS + MalF (G478-D515) | This study | |
| pFH359 | pLysSBAD | DsbBH$_5^{1/8}$; DsbB (M1-F168) R5N, K68Q, R72N + GS + MalF (G478-D515) | This study | |
| pFH343 | pLysSBAD | H$_0$DsbBH$^{3/9}$; MalF (M1-G38) + PW + DsbB (R14-F168) | This study | |

TABLE 2-continued

Plasmid vectors used in this study. Pictorial representations of the transmembrane proteins are shown in each case with the active site face uppermost and positively charged residues (K + R) indicated by black circles.

| Plasmid | Vector | Encodes | Source | Representation |
|---|---|---|---|---|
| pFH344 | pLysSBAD | H$_0$DsbBH$^{2/9}$; MalF (M1-G38) + PW + DsbB (R14-F168) K68Q | This study | 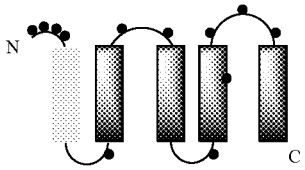 |
| pFH347 | pLysSBAD | H$_0$DsbBH$^{1/9a}$; MalF (M1-G38) + PW + DsbB (R14-F168) K68Q, R72N | This study | 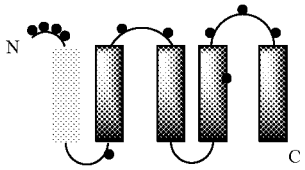 |
| pFH272 | pLysSBAD | H$_0$DsbBH$^{1/9b}$; MalF (M1-G38) + PW + DsbB (R14-F168) K68N, R72N | This study | 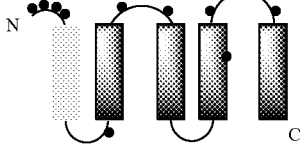 |
| pFH265 | pET23 | MH$_6$-H$_0$DsbB$^{1/9b}$; MalF (M1-G38) + PW + DsbB (R14-F168) K68N, R72N | This study | 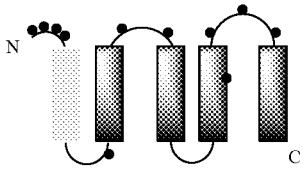 |
| pFH269 | pET23 | MH$_6$-H$_0$DsbB$^{1/9b}$; MalF (M1-G38) + PW + DsbB (R14-F168) C46A, K68N, R72N | This study | 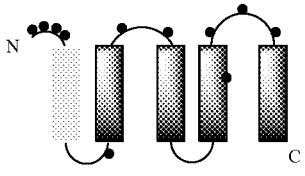 |

For expression in BL21(DE3), cDsbA (A20-K208), with an N-terminal MHHHHHHM-tag (tag sequence SEQ ID NO:19) was cloned (5'XbaI/3'XhoI) into pVD80 (Nguyen et al. 2011) a pET23a derived plasmid which encodes for cPhoA (R22-K271, with an N-terminal MHHHHHHM-tag) (5'SpeI/3' XhoI) to give a bicistronic plasmid pFH258 with expression under a T7 promoter.

Expression in other E. coli strains under a lac promoter/repressor was based on using a modified version of pMALc2x (New England Biolabs). First, a SpeI site was introduced upstream of the start of MBP gene to give pFH313. The bicistronic DNA fragment coding for cPhoA and cDsbA was cloned (5' XbaI/3' XhoI) from pFH258 into pFH313 (5'SpeI/3' SalI). This replaces the original ribosome binding site and MBP gene of pFH313 with cPhoA and cDsbA each preceded by a ribosome binding site carried along from pFH258.

For expression of DsbB and VKOR variants we wanted a low copy plasmid that is compatible for cotransformation with pFH258 or pFH314. We used pLysS (Promega) as the backbone and cloned into it pBAD/araC as described (Nguyen et al. 2011). The gene encoding DsbB was amplified by colony PCR from the E. coli strain BL21 and cloned into this vector (5'NdeI/3'XhoI) and into pET23. The longer DsbB variant in the database (AAA23711.1), encoding a 178 amino acid protein was chosen as the template. The shorter variant is 176 amino acids in length and lacks the first two amino acids Met-Ile. Lysine and arginine residues in cytoplasmic loops were mutated individually (R5N, R14N, K68N, K68Q and R72N) or in combination along with the active site cysteine (C46A) using the QuikChange site-directed mutagenesis kit (Stratagene) according to the manufacturers' instructions. The first and last TMH of E. coli MalF (M1-G38) and (G478-D515) were amplified by PCR and cloned in-frame either 5'BglII/3'NcoI or 5'BamHI/3'XhoI into vectors harboring DsbB variants. This adds the two amino acids PW or GS before the start or after the end of DsbB variant, respectively. apVKOR1 and apVKOR2 were amplified by PCR from the genomic DNA of Aeropyrum Pernix (DSM 11879, German Collection of Microorganisms and Cell Cultures) and cloned into the pLysSBAD vector (5'NdeI/3'XhoI). All plasmids were sequenced to ensure no PCR or cloning errors prior to use.

TABLE 3

Subcellular fractionation of BL21(DE3) E. coli strains expressing $H_0DsbB^{1/9b}$. Absorbance of hydrolyzed ONPG (0.4 mg/ml), Nitrocefin (0.1 mg/ml) and PNPP (1 mg/ml) was measured over time at 420, 486 and 410 nm respectively.

| Marker | Fraction | cPhoA + cDsbA co-expression (mAU/min) | cPhoA co-expression (mAU/min) |
|---|---|---|---|
| β-galactosidase | Total | 9.43 ± 0.01 | 6.29 ± 0.32 |
| β-galactosidase | Cytoplasmic | 9.88 ± 1.02 | 6.11 ± 0.50 |
| β-galactosidase | Periplasmic | 0.00 ± 0.00 | 0.00 ± 0.00 |
| β-lactamase | Total | 35.1 ± 0.8 | 34.9 ± 1.4 |
| β-lactamase | Cytoplasmic | 0.92 ± 0.08 | 1.04 ± 0.02 |
| β-lactamase | Periplasmic | 29.6 ± 1.6 | 30.6 ± 1.1 |
| cPhoA | Total | 26.2 ± 3.9 | 1.77 ± 0.03 |
| cPhoA | Cytoplasmic | 20.3 ± 3.8 | 0.24 ± 0.01 |
| cPhoA | Periplasmic | 0.84 ± 0.22 | 0.59 ± 0.17 |

Data represents mean ± sd ( n = 2).

Motility Assay:

A single colony from JW5182 strain carrying DsbB constructs was stabbed into a motility plate (M63 salts, 1 mM $MgSO_4$, 50 μg/ml thiamine, 0.4% glycerol, 0.1% N—Z-Case plus (Sigma), 0.3% (w/v) agar, 0.0001% arabinose and appropriate antibiotics. Motility halos were examined after 48 hours growth at 30° C.

Alkaline Phosphatase Activity:

For endogenous pPhoA cells transformed with pLysSBAD harboring different mutants of DsbB were grown in 5 ml fresh MOPS media (MOPS salts (Sambrook and Russell, 2001), 50 μg/ml thiamine, 1 mM $MgSO_4$, 0.5% glycerol, 0.2% N—Z-Case plus (Sigma), 0.0001% arabinose, 35 μg/ml chloramphenicol) without addition of phosphate in order to induce chromosomal expression of PhoA. After 14 hours of growth cells were collected by centrifugation and resuspended in lysis buffer (50 mM Tris pH 8.0, 50 mM NEM, 20 μg/ml DNase and 0.1 mg/ml egg white lysozyme) to give a suspension equivalent to $OD_{600}$ of 1 based on the final $OD_{600}$ of the culture and then frozen.

For exogenous cPhoA activity in the E. coli strain FSH8 which is deficient in DsbB, 5 ml pre-cultures, containing suitable antibiotics, were used to seed a 20 ml culture of LB in a 125 ml flask to an $OD_{600}$ of 0.05. This was then grown at 37° C., 200 rpm until the $OD_{600}$ reached 0.4 when expression from pLysSBAD was induced with 0.5% arabinose and 0.08% glucose. 30 minutes later, expression from the pMal plasmid was induced with 1 mM IPTG and cells harvested after 3 hours. The rationale behind including 0.08% glucose is that expression of the transmembrane protein DsbB can be toxic causing growth cessation (Badwer et al., 1998). The addition of glucose brings on catabolite repression of the pBAD promoter (Miyada et al., 1984) and thereby reduces expression of DsbB. The combination of arabinose and glucose at specific ratios proved to be very useful to regulate expression of DsbB from the pBAD promoter without causing growth defects (Table 4). Harvested cells were resuspended in lysis buffer as above and frozen. A similar protocol was used for exogenous cPhoA activity in the E. coli strain BL21(DE3) except that the DsbB constructs were induced first with either 10 μM IPTG (pET23) or 0.5% arabinose (pLysSBAD), with cPhoA and cDsbA being induced 30 minutes later with 1 mM IPTG (pET23) or 0.5% arabinose (pLysSBAD).

TABLE 4

Modulation of expression from pBAD promoter by catabolite repression using glucose. E. coli strain FSH8 harbouring plasmids pFH347 ($H_0DsbB^{1/9a}$) and pFH314 (cPhoA + cDsbA) was induced with arabinose and glucose at $OD_{600}$ = 0.4 and 30 mintues later with 1 mM IPTG. cPhoA activity was measured 3 hours after induction.

| Inducer | cPhoA activity (mAU/min) | Final $OD_{600}$ |
|---|---|---|
| 0.5% arabinose/0.08% glucose | 62.0 ± 1.7 | 2.95 ± 0.06 |
| 0.4% arabinose/0.05% glucose | 54.4 ± 2.7 | 2.98 ± 0.01 |
| 0.01% arabinose/0.08% glucose | 29.3 ± 1.7 | 3.75 ± 0.03 |
| 0.01% arabinose | 3.30 ± 1.2 | 0.60 ± 0.01 |
| 0.5% arabinose | 2.57 ± 0.22 | 0.67 ± 0.05 |

Data represents mean ± sd (n = 2).

Alkaline phosphatase activity for cPhoA and pPhoA samples was measured in a continuous assay by monitoring $\Delta A_{410}$ upon the hydrolysis 4-nitrophenyl phosphate (0.1% w/v in 1 M Tris pH 8.0) with a plate reader using 5 μl of cleared lysate and 195 μl of substrate in a 96 well plate at 25° C.

Cell Fractionation:

For cell fractionation studies none of the ΔdsbB strains could be used as they all lack β-galactosidase. Instead BL21 (DE3) cells, which are lacZ$^+$, harboring the plasmid pFH272 encoding $H_0DsbB^{119}$ with either pFH258 (encoding cPhoA and cDsbA) or pVD80 (encoding cPhoA) were grown in LB as above except that cells were collected 2 h post IPTG induction. 1 ml of culture was spun down and the cell pellet resuspended in 0.5 ml of 20% sucrose buffer containing 33 mM Tris pH 8.0, 1 mM EDTA and 50 mM NEM and left at RT for 10 min. The cells were then spun down at 4000 g for 5 min at +4° C., the supernatant discarded and the cells resuspended in ice-cold 5 mM $MgSO_4$ to give an $OD_{600}$ equivalent of 5 and left on ice for 20 minutes. A 100 μl sample was removed and marked as total, and another 100 μl was spun down at 10000 g for 10 min and the periplasmic content removed to a new tube. The pellet was resuspended to the original volume with 5 mM $MgSO_4$. 20 μg/ml DNase, 0.1 mg/ml lysozyme and 50 mM Tris pH:8.0 were added to all fractions and then freeze-thawed twice. Subsequently activities of β-galactosidase (Miller, 1992), β-lactamase (O'Callaghan et al. 1972), and alkaline phosphatase (as above) were determined.

Bioinformatics Phylogenic Analyses

Accession numbers of PF02600 and PF07884 family members were collected from Pfam and used to retrieve full sequences from Uniprot. Sequences that appeared to lack catalytic cysteines were excluded and the remaining sequences were run on SCAMPI to predict transmembrane regions and topology and selected sequences were further analysed by TOPCONS. We further examined all VKOR homologues from thermophiles by BLASTing apVKOR2 within Archaea. Blast results were aligned using ClustalW2.

TABLE 5

Species containing VKOR homologues that are predicted to have cytoplasmic localization of their catalytic sites. Each of the hyperthermophiles are predicted to have two VKOR homologues with opposite topologies.

| Organism | Accession number | Predicted topology of active site |
|---|---|---|
| Aeropyrum pernix | Q9Y922 | Periplasmic |
| Aeropyrum pernix | Q9YB70 | Cytoplasmic |
| Pyrobaculum aerophilum | Q8ZV09 | Periplasmic |
| Pyrobaculum aerophilum | Q8ZXF9 | Cytoplasmic |

TABLE 5-continued

Species containing VKOR homologues that are predicted to have cytoplasmic localization of their catalytic sites. Each of the hyperthermophiles are predicted to have two VKOR homologues with opposite topologies.

| Organism | Accession number | Predicted topology of active site |
|---|---|---|
| Pyrobaculum arsenaticum | A4WKP9 | Periplasmic |
| Pyrobaculum arsenaticum | A4WI60 | Cytoplasmic |
| Pyrobaculum calidifontis | A3MSV5 | Periplasmic |
| Pyrobaculum calidifontis | A3MVJ3 | Cytoplasmic |
| Pyrobaculum islandicum | A1RVU0 | Periplasmic |
| Pyrobaculum islandicum | A1RVC9 | Cytoplasmic |

Example 2

A list of all of the plasmid vectors used in this study is shown in Table 6.

TABLE 6

Plasmid vectors used in this study

| Plasmid | Vector | Encodes | Source |
|---|---|---|---|
| pFH277 | pLysSBAD | Nothing | This study |
| pFH371 | pLysSBAD | apVKOR1 (Met1-Thr145) | This study |
| pFH372 | pLysSBAD | apVKOR2 (Met1-Gly147) | This study |
| pFH272 | pLysSBAD | H$_0$DsbB$^{1/9b}$; MalF (M1-G38) + PW + DsbB (R14-F168) K68N, R72N | This study |
| pVD171 | pET23 | Mature E. coli MBP (Lys27-Thr392) plus a linker GSGSGSGSGSIEGRGSGSGSGSGSHM-vtPA (Gly211-Pro562) (linker SEQ ID NO: 20) | (Nguyen et al, 2011) |
| pMJS41 | pET23 | Mature E. coli MBP (Lys27-Thr392) plus a linker GSGSGSGSGSIEGRGSGSGSGSGSHM-vtPA (Gly211-Pro562) and cDsbC (D21-K236) and cDsbA (A20-K208) (linker SEQ ID NO: 21) | This study |

The polycistronic vectors pMJS41 was constructed by taking a fragment encoding cDsbA from a pET23 based constructs by XbaI/XhoI digest (which includes the ribosome binding site) and ligating the fragment into SpeI/XhoI cut pVD171. This generates a plasmid that contains a single transcription initiator/terminator and hence makes a single mRNA, but has three ribosome binding sites and makes three proteins by co-expression from three translation initiation sites.

For expression in LB media, E. coli strains containing expression vectors were streaked out from glycerol stocks stored at −70° C. onto LB agar plates containing suitable antibiotics to allow for selection (100 µg/ml ampicillin for pET23 derivatives, 35 µg/ml chloramphenicol for pLysS derivatives; with 10 µg/ml tetracycline and 15 µg/ml kanamycin for selection of origami strain). The next day one colony from these plates were used to inoculate 5 ml of LB media, containing suitable antibiotics, and grown overnight at 30° C., 200 rpm. This overnight culture was used to seed a 50 ml culture of LB containing suitable antibiotics in a 250 ml conical flask to an optical density of 0.05 at 600 nm (OD$_{600}$). This culture was grown at 30° C., 200 rpm until the OD$_{600}$ reached 0.4 at which point production of protein from pLysS-BAD vectors was induced by the addition of 0.5% w/v arabinose followed 30 minutes later by the induction of proteins from pET23 vectors with 0.5 mM IPTG. The cells were then grown for a total of 4 hours post induction at 30° C., 200 rpm and the final OD$_{600}$ measured. The cells were collected by centrifugation and resuspended to an OD$_{600}$ equivalent of 10 (based on the final OD$_{600}$ of the culture) in 20 mM sodium phosphate pH 7.4, 20 µg/ml DNase, 0.1 mg/ml egg white lysozyme and frozen. Such normalization allows for easy correction for differences in the growth rates of the cultures and allows rapid equal total protein loading of samples for activity assay. Cells were lysed by freeze-thawing. The insoluble fraction was removed by centrifugation and the soluble fraction removed quickly to a new container.

vtPA activity was measured using a chromagenic substrate, chromozyme t-PA peptide assay (Roche), using a methodology similar that that recommended by the manufacturer but adapted for a continuous assay in 96-well plate format. Since this method showed slight variations in activity with time all of the vtPA activity measurements were repeated using the same batch of substrate and same buffers and that data is presented here. 20 mg of substrate was dissolved in 4 ml of sterilized water to generate a 20× substrate stock solution. 20 µl of soluble fraction from cell lysates were added to 180 µl of substrate diluted in reaction buffer (100 mM tris-HCl, 0.15% tween20; pH 8.5) to give a final concentration that is 1× in a 96 well microtitre plate, thermally equilibrated to 37° C. The absorbance at 405 nm was measured at 3 minute intervals for 30 minutes to determine the rate of formation of the product. All samples were measured in duplicate.

REFERENCES

J. H. Miller, *A Short Course in Bacterial Genetics* (Cold Spring Harbor Laboratory Press, Cold Spring Harbor, N.Y., 1992).

V. D. Nguyen et al., *Microb. Cell Fact.* 10, 1 (2011)

J. Sambrook, D. W. Russell, *Molecular Cloning: A Laboratory Manual* (Cold Spring Harbor Laboratory Press, Cold Spring Harbor, N. Y., ed. 3, 2001).

M. Bader, W. Muse, T. Zander, J. Bardwell, *J. Biol. Chem.* 273, 10302 (1998).

C. G. Miyada, L. Stoltzfus, G. Wilcox, *Proc. Natl. Acad. Sci. U.S.A.* 81, 4120 (1984).

C. H. O'Callaghan, A. Morris, S. M. Kirby, A. H. Shingler, *Antimicrob. Agents Chemother.* 1, 283 (1972)

B. J. Wallace, I. G. Young, *Biochim. Biophys. Acta* 461, 84 (1977)

---

The invention claimed is:

1. A method for producing disulfide bond containing recombinant eukaryotic or prokaryotic proteins in gram negative bacterial cells, said method comprising the step of
expressing in the cytoplasm of the bacterial cell
a eukaryotic or a prokaryotic protein of interest that naturally contains two or more disulfide bonds;
an inverted VKOR (Vitamin K Oxidoreductase) transmembrane enzyme or an inverted DsbB transmembrane enzyme capable of catalysing process of native disulphide bond formation by catalysing reaction Dithiol+Quinone→Disulfide+Quinol, said inverted transmembrane enzyme having an active site comprising at least four cysteine residues located toward the bacterial cytoplasm, and said inverted transmembrane enzyme being obtained by removing or adding one or more cytoplasmic lysine and/or arginine residues from naturally occurring VKOR or DsbB proteins, wherein the removal or addition of one or more lysine and/or arginine residues changes the charge distribution of the transmembrane enzyme thereby causing inversion of the enzyme topology such that the cysteines of the active site locate toward the bacterial cytoplasm;
wherein the DsbB enzyme has PFAM Accession number PF02600 and VKOR has PFAM Accession number PF07884;
and
a cytoplasmic DsbA being capable of providing electrons to the active site(s) of the inverted VKOR, or the inverted DsbB,
whereby natively folded disulfide bond containing protein of interest is formed in the bacterial cytoplasm.

2. The method according to claim 1, wherein the DsbB or the VKOR is fused to a transmembrane helix or transmembrane helices of another transmembrane protein.

3. The method according to claim 2, wherein the another transmembrane protein is maltose transporter MalF or Leader peptidase Lep.

4. The method according to claim 1, wherein the one or more cytoplasmic lysine and/or arginine residues are removed by mutagenesis or deletion of positively charged N- and/or C-terminus of the DsbB or VKOR protein.

5. The method according to claim 1, wherein the method further comprises expressing in the bacterial cytoplasm host cell a thiol-disulfide isomerase.

6. The method according to claim 1, wherein the bacterium is E. coli.

7. A method for producing a gram negative bacterial host cell for producing eukaryotic or prokaryotic recombinant protein(s) of interest containing at least two disulfide bonds, said method comprising genetic engineering of the host cell to express in the cytoplasm an inverted VKOR (iVKOR) or an inverted DsbB (iDsbB) transmembrane enzyme catalysing the process of native disulfide bond formation by catalysing reaction Dithiol+Quinone→Disulfide+Quinol,
said inverted transmembrane enzyme having an active site comprising at least four cysteine residues located toward the bacterial cytoplasm, and said inverted transmembrane enzyme being obtained by removing or adding one or more cytoplasmic lysine and/or arginine residues from naturally occurring VKOR having PFAM Accession number PF07884, or DsbB having PFAM Accession number PF07884, wherein the removal or addition of one or more lysine and/or arginine residues changes the charge distribution of the transmembrane enzyme thereby causing inversion of the enzyme topology such that the cysteines of the active site locate toward the bacterial cytoplasm and
a cytoplasmic DsbA being capable of providing electrons to the active site(s) of the iVKOR or iDsbB,
whereby the bacterial host cell is capable of forming natively folded disulfide bond containing eukaryotic or prokaryotic recombinant protein(s) of interest in the cytoplasm.

8. A gram negative bacterial host cell genetically engineered to express
an inverted VKOR (iVKOR) transmembrane enzyme or an inverted DsbB (iDsbB) transmembrane enzyme catalysing-process of native disulfide bond by catalysing reaction Dithiol+Quinone→Disulfide+Quinol and, said inverted transmembrane enzymes having cystein residues of their active sites toward the cytoplasm, and wherein the iVKOR is obtained from a naturally occurring VKOR having PFAM accession number PF0788 and having at least four cysteine residues in its active site, and the iDsbB is obtained from naturally occurring DsbB having PFAM accession number PF02600 and having at least four cysteine residues in its active site, and
a cytoplasmic DsbA protein being capable of providing electrons to the active site(s) of, the iVKOR or iDsbB,
said host cell being capable of forming in the cytoplasm natively folded eukaryotic or prokaryotic recombinant protein(s) of interest containing at least two disulfide bonds.

9. The host cell according to claim 8, wherein the host further expresses in the cytoplasm a thiol-disulfide isomerase.

10. The host cell of claim 8, wherein the bacterium is E. coli.

11. The host cell according to claim 8, wherein a nucleic acid sequence encoding the inverted VKOR (iVKOR) or the inverted DsbB (iDsbB) is chromosomally integrated or is in a vector.

12. The host cell according to claim 8, wherein a nucleic acid sequence encoding DsbA capable of providing electrons to the active site(s) of the iVKOR or the iDsbB, or a nucleic acid sequence encoding a thiol-disulfide isomerase is chromosomally integrated or is in a vector.

13. A vector system comprising:
a vector encoding
a) an inverted transmembrane enzyme iVKOR or iDsbB, said inverted transmembrane enzyme being genetically modified to have cysteines of its active site(s) located towards bacterial cytoplasm, and said enzyme being capable of catalyzing process of native disulfide bond formation by catalysing reaction Dithiol+Quinone→Disulfide+Quinol, and
b) a cytoplamic DsbA being capable of providing electrons to the active site(s) of iVKOR or iDsbB, and optionally having a site for a nucleic acid sequence encoding eukaryotic or prokaryotic recombinant protein(s) of interest, or
a first vector encoding iVKOR or iDsbB, and
a second vector encoding cytoplasmic DsbA being capable of providing electrons to the active site(s) of iVKOR or iDsbB,
said first or said second vector optionally having a site for a nucleic acid sequence encoding eukaryotic or prokaryotic recombinant protein(s) of interest.

14. The vector system according to claim 13, wherein one of the vectors further encodes cytoplasmic thiol-disulfide isomerase.

15. The method of claim 1, wherein the DsbB enzyme has an amino acid sequence with at least 70% identity to a sequence selected from the group consisting of SEQ ID NOs 1-7 and the VKOR enzyme has an amino acid sequence with at least 70% identity to a sequence selected from the group consisting of SEQ ID NOs 8-15.

16. The method according to claim 1, wherein the DsbA protein—has a sequence according to accession number CAA56736 or AAA23715.

17. The method of claim 5, wherein the thiol-disulfide isomerase is DsbC protein having a sequence according to accession number AAA83047 or AAC75931, or PDI protein having a sequence according to accession number CAA42373, BAA00723, CAA38402, CAA28775, or AAC13652.

18. The method of claim 7, wherein the method further comprises expressing in the cytoplasm of the host cell a thiol-disulfide isomerase.

19. The method of claim 7, wherein a nucleic acid sequence encoding the inverted VKOR (iVKOR) or the inverted DsbB (iDsbB) is chromosomally integrated into the host cell or is in a vector.

20. The method of claim 7, wherein a nucleic acid sequence encoding DsbA protein being capable of providing electrons to the actives site(s) of iVKOR or iDsbB, or a nucleic acid sequence encoding a thiol-disulfide isomerase, is chromosomally integrated into the host cell or is in a vector.

\* \* \* \* \*